United States Patent
Tal et al.

(10) Patent No.: US 11,931,042 B2
(45) Date of Patent: Mar. 19, 2024

(54) PREVENTING NON-TARGET EMBOLIZATION

(71) Applicant: ACCURATE MEDICAL THERAPEUTICS LTD., Tel-Aviv (IL)

(72) Inventors: Michael Gabriel Tal, Savyon (IL); Eran Miller, Moshav Beit Elazari (IL)

(73) Assignee: ACCURATE MEDICAL THERAPEUTICS LTD., Tel-Aviv (IL)

(*) Notice: Subject to any disclaimer, the term of this patent is extended or adjusted under 35 U.S.C. 154(b) by 321 days.

(21) Appl. No.: 17/243,996

(22) Filed: Apr. 29, 2021

(65) Prior Publication Data
US 2021/0259703 A1 Aug. 26, 2021

Related U.S. Application Data

(62) Division of application No. 15/554,772, filed as application No. PCT/IB2016/051186 on Mar. 2, 2016, now abandoned.
(Continued)

(51) Int. Cl.
*A61B 17/12* (2006.01)
*A61K 9/00* (2006.01)
(Continued)

(52) U.S. Cl.
CPC .. *A61B 17/12181* (2013.01); *A61B 17/12109* (2013.01); *A61B 17/12186* (2013.01);
(Continued)

(58) Field of Classification Search
CPC ........ A61B 17/12109; A61B 17/12181; A61B 17/12186; A61B 2017/1205;
(Continued)

(56) References Cited

U.S. PATENT DOCUMENTS

| | | | |
|---|---|---|---|
| 5,735,289 A | 4/1998 | Pfeffer et al. | |
| 5,941,896 A * | 8/1999 | Kerr | A61F 2/0105 606/192 |

(Continued)

FOREIGN PATENT DOCUMENTS

| | | |
|---|---|---|
| WO | 9855175 A1 | 12/1998 |
| WO | 03034941 A1 | 5/2003 |
| WO | 2004083817 A2 | 9/2004 |

OTHER PUBLICATIONS

International Search Report of PCT/IB2016/051186 Completed Jul. 5, 2016; dated Jul. 11, 2016 8 pages.
(Continued)

*Primary Examiner* — Mohamed G Gabr
(74) *Attorney, Agent, or Firm* — The Roy Gross Law Firm, LLC; Roy Gross

(57) ABSTRACT

Devices, methods and kits for preventing or reducing non-target microparticles deposition and embolization, in conjunction with delivering microparticles (e.g., embolization material) via a blood vessel to a target bodily part. Applicable for entrapping infiltrated microparticles within heart right atrium. Entrapping device includes: filter; and filter collapsing mechanism sized for positioning in catheter lumen of a filter delivering catheter, and having proximal end actuatable from outside of subject. Filter configured for positioning within heart right atrium, for self-expanding and covering right atrium inlet opening, and configured, when expanded, to collect embolic material delivered to target organ and infiltrated into outflow vessel thereof draining to right atrium. Filter collapsing mechanism configured for collapsing, and being manipulated to form a pocket in filter, to entrap collected embolic material therein, and drawing filter with collected embolic material in pocket, into catheter lumen of filter delivering catheter.

16 Claims, 15 Drawing Sheets

Related U.S. Application Data

(60) Provisional application No. 62/127,036, filed on Mar. 2, 2015.

(51) Int. Cl.
*A61K 9/16* (2006.01)
*A61K 31/704* (2006.01)
*A61L 24/00* (2006.01)
*A61L 24/02* (2006.01)
*A61M 5/00* (2006.01)
*A61M 25/00* (2006.01)
*A61F 2/01* (2006.01)

(52) U.S. Cl.
CPC .......... *A61K 9/0019* (2013.01); *A61K 9/1676* (2013.01); *A61K 31/704* (2013.01); *A61L 24/0015* (2013.01); *A61L 24/02* (2013.01); *A61M 25/0074* (2013.01); *A61B 2017/1205* (2013.01); *A61F 2/011* (2020.05); *A61F 2002/016* (2013.01); *A61L 2300/23* (2013.01); *A61L 2300/416* (2013.01); *A61L 2430/36* (2013.01); *A61M 5/007* (2013.01); *A61M 25/0021* (2013.01); *A61M 2025/0042* (2013.01); *A61M 25/007* (2013.01)

(58) Field of Classification Search
CPC .......... A61F 2002/011; A61F 2002/016; A61F 2/013; A61M 2025/0042; A61M 25/0021; A61M 25/007; A61M 25/0074; A61M 5/007

See application file for complete search history.

(56) References Cited

U.S. PATENT DOCUMENTS

| | | | |
|---|---|---|---|
| 5,957,901 A * | 9/1999 | Mottola | A61M 25/007 604/269 |
| 6,610,077 B1 | 8/2003 | Hancock et al. | |
| 2001/0041909 A1 | 11/2001 | Tsugita et al. | |
| 2002/0095171 A1 | 7/2002 | Belef | |
| 2003/0045842 A1* | 3/2003 | Kawakita | A61M 25/007 604/264 |
| 2003/0114879 A1 | 6/2003 | Euteneuer et al. | |
| 2003/0130680 A1 | 7/2003 | Russell | |
| 2003/0176884 A1 | 9/2003 | Berrada et al. | |
| 2004/0153118 A1 | 8/2004 | Clubb et al. | |
| 2006/0229660 A1 | 10/2006 | Pal et al. | |
| 2010/0049165 A1* | 2/2010 | Sutherland | A61B 17/12109 604/529 |
| 2011/0160763 A1* | 6/2011 | Ferrera | A61F 2/82 606/200 |
| 2014/0364835 A1* | 12/2014 | Allen | A61M 25/0075 604/102.03 |

OTHER PUBLICATIONS

Written Opinion of PCT/IB2016/051186 Completed Jul. 5, 2016; dated Jul. 11, 2016 9 pages.

* cited by examiner

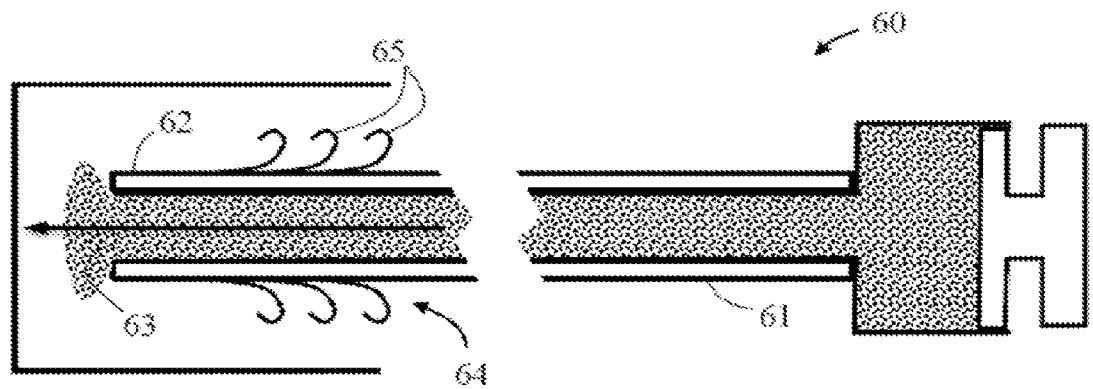
FIG. 7A
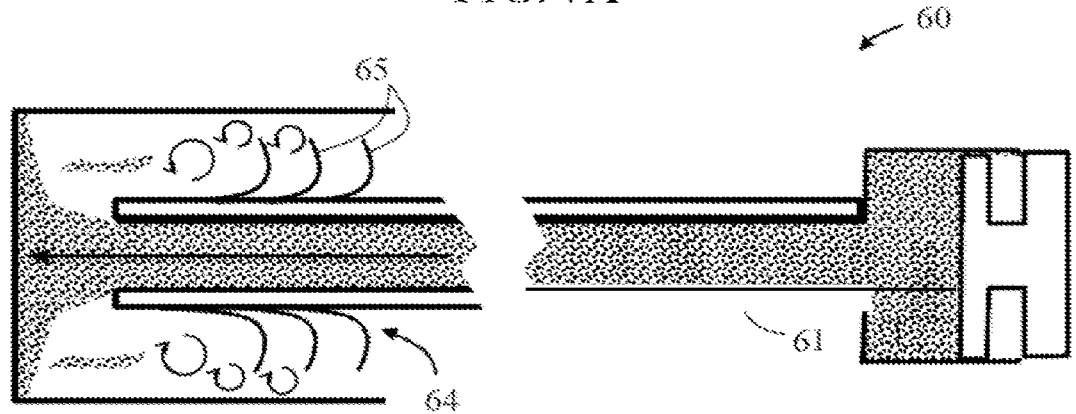
FIG. 7B
FIG. 8A
FIG. 8B
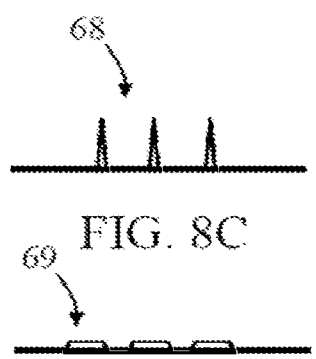
FIG. 8C
FIG. 8D

PREVENTING NON-TARGET EMBOLIZATION

RELATED APPLICATIONS

This application is divisional of U.S. patent application Ser. No. 15/554,772, filed on Aug. 31, 2017, which is a 35 U.S.C. § 371 national phase application of PCT/IB2016/051186, filed Mar. 2, 2016, which claims the benefit of priority under 35 USC 119(e) of U.S. Provisional Patent Application 62/127,036, filed on Mar. 2, 2015 entitled "Emobilization Microcatheter and Uses Thereof", the contents of which are all incorporated herein by reference in their entirety.

FIELD OF THE INVENTION

The present invention, in some embodiments thereof, relates to devices, methods, and kits for preventing or reducing non-target microparticles deposition and embolization, in conjunction with delivering microparticles (e.g., an embolization material) via a blood vessel to a target bodily part. Some embodiments of the invention relate to devices and methods for entrapping infiltrated microparticles within the heart right atrium.

BACKGROUND OF THE INVENTION

The purpose of embolization therapy is to prevent blood flow to an area of the body. Embolization therapy can effectively shrink a tumor or block an aneurysm, and is commonly carried using an endovascular catheter. Access to the organ in question is acquired by means of a guidewire and catheter(s). The position of the correct artery or vein supplying the pathology in question can be located by digital subtraction angiography (DSA), producing images are then used as an accessing map to the correct vessel. An artificial embolus can be formed when using coils, particles, foam, plug, microspheres or beads, as an embolization material.

Transarterial embolization therapy, tumor embolization, or transcatheter arterial embolization (TAE), involves administration of embolization material (which may include chemotherapeutics or/and radiotherapeutics) directly to a tumor typically associated with a target bodily part, such as an organ (for example, the liver), via a catheter. These techniques are usually performed using a microcatheter which targets the tumor, while attempting to avoid dispersion of embolization material to healthy organs.

One of the problems associated with embolization therapy is commonly known as "non-target embolization", where the embolic material travels along small blood vessels, other than those which directly feed the target tumor or region. Non-target embolization is partly caused by shunts that are commonly formed in cancers at advanced stages and that bypass existing capillary bed to integrate the blood circulation.

For example, embolization liver therapy is a procedure associated with the insertion of a catheter into the hepatic artery and injection of embolization material. The embolization material may include chemotherapeutics or radiotherapeutics which may infiltrate also to sensitive tissues and organs, such as to the lungs, through arteriovenous shunts. This can damage healthy tissues in these areas, often resulting in serious complications. Specific serious complications and toxicities are associated with radioembolization. This technique may be associated with non-target deposition of embolic material comprising yttrium-90 ($^{90}Y$) in tissues such as healthy liver tissue, stomach, bowel, and lungs. Such non-target deposition may, for example, cause a liver disease when deposition of the embolic material is within healthy or functional liver, ulceration when deposition of the embolic material is within the stomach or bowel, and radiation pneumonitis (RP) when deposition of the embolic material is within the lungs.

Another problem associated with embolization therapy is reflux or backflow of the embolic material during the embolization procedure. Reflux is a potential complication which can result in occlusion of distal vascular beds. The conditions under which reflux was demonstrated include (1) low flow states, (2) overvigorous flushing, (3) selective contrast injections, and (4) placement of embolic material too proximally.

In view of the preceding, and other limitations associated with current embolization techniques, there is a need for developing and practicing improved or/and new techniques for delivering embolization material into small blood vessels located in close proximity to a target body part, while diminishing or preventing non-target embolic material deposition and embolization.

SUMMARY OF THE INVENTION

The present invention, in some embodiments thereof, relates to devices, methods, and kits for preventing or reducing non-target microparticles deposition and embolization, in conjunction with delivering microparticles (e.g., an embolization material) via a blood vessel to a target bodily part. Some embodiments of the invention relate to devices and methods for entrapping infiltrated microparticles within the heart right atrium.

In some embodiments, the present invention provides methods, kits and devices for reducing or preventing non-target delivery of an embolic material by capturing embolic material infiltrated to the blood circulation from a body organ outflow. In further embodiments, the invention relates to embolic material entrapping devices configured for positioning within a blood vessel, downstream to a target body organ, or within a non-target body organ, for capturing embolic material infiltrated to a body organ outflow. In yet further embodiments, the present invention may provide a solution to the problem of non-target embolization that may be associated, for example, with shunting (e.g., pulmonary shunting) phenomena or/and reflux phenomena.

By providing means and methods to entrap embolic material within a non-target body organ or a blood vessel, some embodiments of the present invention may provide for a safe embolization therapy and allow utilizing this technique also within a patient population that has been otherwise prohibited from embolization therapy or that has been limited to a reduced therapeutic dosage of embolic material.

According to an aspect of some embodiments of the present invention there is provided an entrapping device for preventing or reducing non-target deposition of embolic material following embolization therapy in a blood vessel feeding a target organ in a subject, the entrapping device comprising: a filter; and a filter collapsing mechanism, sized for being positioned in a catheter lumen of a filter delivering catheter, and having a proximal end actuatable from outside of the subject; wherein the filter is configured for positioning within a heart right atrium via an inlet opening of the right atrium, and, for self-expanding and covering the right atrium inlet opening from within the right atrium, and is sized and configured such that, when expanded, the filter collects the embolic material delivered to the target organ and infiltrated into an outflow vessel of the target organ draining to the right atrium; and wherein the filter collapsing mechanism is configured for collapsing, and for being manipulated into forming a pocket in the filter, so as to entrap the collected embolic material in the pocket, and for drawing the filter with the collected embolic material in the pocket, into the catheter lumen of the filter delivering catheter.

According to some embodiments of the invention, the filter collapsing mechanism includes: an elongated tubular body connectable with a distal end to the filter; and a drawstring extendable from an opened proximal perimeter of the filter to outside of the subject, wherein the drawstring is passable within the elongated tubular body; wherein the filter collapsing mechanism is configured for the collapsing and the being manipulated by pulling the drawstring away from the filter against the elongated tubular body.

According to some embodiments of the invention, the filter has a cap-shape structure sized and configured to seal the inlet opening of the heart right atrium.

According to some embodiments of the invention, the entrapping device further comprises a hollow circumferential sleeve connected about a proximally opened perimeter of the filter and configured for housing the drawstring at the proximally opened perimeter of the filter.

According to some embodiments of the invention, the filter delivering catheter is configured for housing the entrapping device in a collapsed configuration. According to some embodiments of the invention, the filter comprises a fine mesh having strands with a thickness of about 200 micrometers or less, or optionally particularly about 100 micrometers or less. According to some embodiments of the invention, the filter comprises pores configured to block passage therethrough of the embolic material and to allow passage therethrough of incoming blood flow.

According to some embodiments of the invention, the embolic material has a diameter equal to or greater than a predetermined size. According to some embodiments of the invention, the predetermined size is within a range of between about 20 micrometers and about 60 micrometers.

According to some embodiments of the invention, the entrapping device is configured for collecting the embolic material in a form of: beads, foam, or gel. According to some embodiments of the invention, the beads are loaded with a radioactive agent or a chemotherapeutic agent.

According to an aspect of some embodiments of the present invention there is provided a method of applying multi-layered protection from non-target embolization or/and non-target deposition of microparticles in a subject, the method comprising: positioning an entrapping device in a first anatomical location downstream to a target organ, the entrapping device is configured to filter the microparticles from blood flow and to entrap the microparticles; placing a distal outlet of a microcatheter in a second anatomical location upstream to the target organ; delivering an infusion suspension including the microparticles via the distal outlet in the second anatomical location upstream to, and towards, the target organ, while allowing a continuous blood flow downstream towards and away from the target organ, by applying a flow disturbance mechanism in the second anatomical location, proximally to the microcatheter distal outlet, thereby creating a local disturbance in blood flow so as to suppress a retrograded flow of the microparticles flowable upstream to the target organ; and removing the entrapping device from the subject following a chosen time, after ceasing of the delivering, sufficient for allowing the entrapping device to entrap infiltrating microparticles infiltratable upstream through the flow disturbance mechanism or/and downstream to the target organ.

According to some embodiments of the invention, the microparticles include, or are included in, embolic material, and are configured for forming emboli.

According to some embodiments of the invention, the chosen time is additionally sufficient for allowing the microparticles to form an embolus in a target blood vessel feeding the target organ, the embolus is sized for occluding the target blood vessel.

According to some embodiments of the invention, the target organ is a liver in the subject. According to some embodiments of the invention, the first anatomical location is a non-target vessel connecting the target organ to a non-target organ and providing blood flow communication therebetween. According to some embodiments of the invention, the non-target vessel is an abnormally formed shunt connecting the target organ to a vein carrying deoxygenated blood towards the subject's heart. According to some embodiments of the invention, the non-target vessel is an inner portion of the heart, such as the right atrium, in the subject.

According to some embodiments of the invention, the second anatomical location is a target blood vessel feeding the target organ.

According to some embodiments of the invention, in the method, placing the distal outlet is performed concomitantly with, following, or before, positioning the entrapping device.

According to some embodiments of the invention, in the method, positioning an entrapping device, comprises: providing a filter delivering catheter, the filter delivering catheter comprises a proximal end, a distal end, and a lumen extending therebetween the ends, and is configured for housing the entrapping device in a collapsed configuration; introducing the filter delivering catheter into the first anatomic location; and deploying the entrapping device to thereby facilitate the positioning.

According to some embodiments of the invention, the entrapping device comprises a filter and a filter collapsing mechanism, the filter collapsing mechanism is sized for being positioned in a catheter lumen of the filter delivering catheter, and has a proximal end actuatable from outside of the subject, and wherein the deploying the entrapping device comprises retracting the filter delivering catheter or/and removing the filter from the catheter lumen using the filter collapsing mechanism.

According to some embodiments of the invention, the method further comprises, prior to introducing the filter delivering catheter, inserting a guidewire for facilitating access and delivery of the filter delivering catheter within a blood vessel, downstream to the target organ or within a non-target organ.

According to some embodiments of the invention, the filter collapsing mechanism includes an elongated tubular body connected with a distal end to the filter, and a drawstring extending from an opened perimeter of the filter and continuously threaded within the elongated tubular body; wherein deploying the entrapping device comprises pushing the elongated tubular body distally, to thereby deploy in an outwardly direction the entrapping device, and wherein removing the entrapping device comprises re-collapsing the entrapping device with entrapped microparticles inwardly within the filter delivering catheter by proximally pulling the drawstring.

According to some embodiments of the invention, the microcatheter comprises: a tubular wall having a proximal wall end, a distal wall end, and a lumen extending between the wall ends, the lumen is opened to the distal outlet at the distal wall end and to a plurality of side openings distributed around or/and along a section of the tubular wall proximally to the distal outlet; the microcatheter is configured to deliver an infusion suspension including the microparticles suspended in an infusion fluid, via the lumen to the distal outlet; wherein the distal outlet is shaped or/and sized to allow passage therethrough of the infusion suspension, and each of the side openings is shaped or/and sized to allow passage therethrough of the infusion fluid without the microparticles and to block passage therethrough of the microparticles.

According to some embodiments of the invention, at least one of the side openings comprises a slit with a gap having a maximal cross sectional dimension less than a minimal diameter of the microparticles. According to some embodiments of the invention, at least one of the side openings comprises a pore having a maximal cross sectional dimension less than a minimal diameter of the microparticles.

According to some embodiments of the invention, in the method, positioning the entrapping device comprises deploying the entrapping device to thereby cover a wall of the first anatomical location, downstream to the target organ. According to some embodiments of the invention, the first anatomical location is a hepatic vein or a portion of the inferior vena cava, above the hepatic vein. According to some embodiments of the invention, the target blood vessel is a small blood vessel directly feeding cancerous tissue of the target organ.

According to an aspect of some embodiments of the present invention there is provided a method for performing local embolization in a blood vessel feeding a target organ in a subject, the method comprising: positioning an entrapping device within a heart right atrium via an inlet opening of the right atrium, the entrapping device is configured to filter embolic material from blood flow, and to entrap the embolic material; deploying the entrapping device to thereby cover the inlet opening of the right atrium from within the right atrium; placing a distal outlet of a microcatheter in the blood vessel feeding the target organ; delivering the embolic material via the distal outlet in the blood vessel towards the target organ; and removing the entrapping device from the subject following a chosen time after ceasing of the delivering, sufficient for allowing the entrapping device to entrap the embolic material infiltratable in the heart right atrium.

According to some embodiments of the invention, in the method, placing the distal outlet of the microcatheter in the blood vessel is performed concomitantly with, following, or before positioning the entrapping device in the blood vessel.

According to some embodiments of the invention, in the method, positioning the entrapping device, comprises: providing a catheter having a proximal end, a distal end, and a lumen extending therebetween the ends, the catheter is configured for housing the entrapping device in a collapsed configuration; and inserting the catheter into the heart right atrium.

According to some embodiments of the invention, the entrapping devices comprises a filter and an elongated tubular body connected with a distal end to the filter, and wherein deploying the entrapping device comprises retracting the catheter proximally or pushing the elongated tubular body distally, to thereby deploy in an outwardly direction the entrapping device.

According to some embodiments of the invention, the method further comprises inserting, prior to introducing the catheter, a guidewire for facilitating access and delivery of the catheter within the blood vessel, downstream to the target organ or within a non-target organ.

According to some embodiments of the invention, the entrapping device further comprises a drawstring extending from an opened perimeter of the filter and continuously threaded within the tubular body, and wherein removing the entrapping device comprises re-collapsing the entrapping device with the entrapped embolic material inwardly within the catheter by proximally pulling the drawstring.

According to some embodiments of the invention, the microcatheter comprises: a tubular wall having a proximal wall end, a distal wall end, and a lumen extending between the wall ends, the lumen is opened to a distal outlet at the distal wall end and to a plurality of side openings distributed around or/and along a section of the tubular wall proximally to the distal outlet; the microcatheter is configured to deliver an infusion suspension of the embolic material in an infusion fluid, via the lumen to the distal outlet; wherein the distal outlet is shaped or/and sized to allow passage therethrough of the infusion suspension, and each of the side openings is shaped or/and sized to allow passage therethrough of the infusion fluid without the embolic material and to block passage therethrough of the embolic material.

According to some embodiments of the invention, at least one of the side openings comprises a slit with a gap having a maximal cross sectional dimension less than a minimal diameter of the embolic material. According to some embodiments of the invention, at least one of the side openings comprises a pore having a maximal cross sectional dimension less than a minimal diameter of the embolic material.

According to an aspect of some embodiments of the present invention there is provided a kit for preventing non-target deposition of embolic material, the kit comprising an entrapping device configured for capturing the embolic material within a blood vessel, downstream to a target organ or a non-target organ, and a microcatheter configured for delivering the embolic material into the blood vessel feeding a bodily organ.

According to some embodiments of the invention, in the kit, the entrapping device comprises: a collapsible filter, an elongated tubular body connected with a distal end to the filter and actuatable with a proximal end thereof from outside the subject body, and a drawstring extended from an opened proximal perimeter of the filter and continuously threaded within an inner lumen of the elongated tubular body; the filter is configured for positioning within a heart right atrium via an inlet opening of the right atrium, and for self-expanding and covering the right atrium inlet opening from within the right atrium, and is sized and configured for collecting the embolic material delivered to the target organ and infiltrated into an outflow vessel of the target organ draining to the right atrium; the drawstring is configured for re-collapsing the filter into forming a pocket, by proximally pulling the drawstring, so as to entrap the collected embolic material in the pocket; and the elongated tubular body is configured for drawing the filter, with the embolic material in the pocket, into a lumen of a catheter.

According to some embodiments of the invention, in the kit, the filter has a cap-shape structure configured to seal the inlet opening of the heart right atrium.

According to some embodiments of the invention, the kit further comprises a hollow circumferential sleeve connected about a proximally opened perimeter of the filter and configured for housing the drawstring at the proximally opened perimeter of the filter. According to some embodiments of the invention, the catheter is configured for housing the entrapping device in a collapsed configuration. According to some embodiments of the invention, the filter comprises a fine mesh having strands with a thickness of no more than 200 micrometers. According to some embodiments of the invention, the filter comprises pores configured to block passage therethrough of an embolic material and to allow passage therethrough of incoming blood flow.

According to some embodiments of the invention, the embolic material is having a diameter that equals to or greater than a predetermined size. According to some embodiments of the invention, the predetermined size is within the range of between 20 micrometers and 60 micrometers.

According to some embodiments of the invention, the kit is configured for collecting an embolic material in the form of: beads, foam, and gel. According to some embodiments of the invention, the catheter is an embolization microcatheter configured to reduce reflux of the embolic material, during continuous delivery thereof in a subject.

According to some embodiments of the invention, the embolization microcatheter comprises: a tubular wall having a proximal wall end, a distal wall end, and a lumen extending between the wall ends, the lumen is opened to a distal outlet at the distal wall end and to a plurality of side openings distributed around or/and along a section of the tubular wall proximally to the distal outlet; the embolization microcatheter is configured to deliver an infusion suspension of the embolic material in an infusion fluid, via the lumen to the distal outlet; wherein the distal outlet is shaped or/and sized to allow passage therethrough of the infusion suspension of the infusion fluid and the embolic material, and each of the side openings is shaped or/and sized to allow passage therethrough of the infusion fluid without the embolic material and to block passage therethrough of the embolic material.

According to some embodiments of the invention, at least one of the side openings comprises a slit with a gap having a maximal cross sectional dimension less than a minimal diameter of the embolic material. According to some embodiments of the invention, at least one of the side openings comprises a pore having a maximal cross sectional dimension less than a minimal diameter of the embolic material. According to some embodiments of the invention, the kit further comprises a vial containing the embolic material.

Unless otherwise defined, all technical or/and scientific terms used herein have the same meaning as commonly understood by one of ordinary skill in the art to which the invention pertains. Although methods and materials similar or equivalent to those described herein can be used in the practice or testing of embodiments of the invention, exemplary methods or/and materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-7B are schematic side cut views of exemplary embodiment of a microcatheter including a plurality of projections, during delivery of embolic material (e.g., embolization material or/and contrast enhancing material) before (FIG. 7A) and after (FIG. 7B) occurrence of a retrograded flow, in accordance with some embodiments of the invention; and FIGS. 8A-8D are schematic partial side cut views of exemplary embodiments of different exemplary projections of an embolic material flow disruption section, in accordance with some embodiments of the invention.

DESCRIPTION OF SPECIFIC EMBODIMENTS OF THE INVENTION

Figure 1:
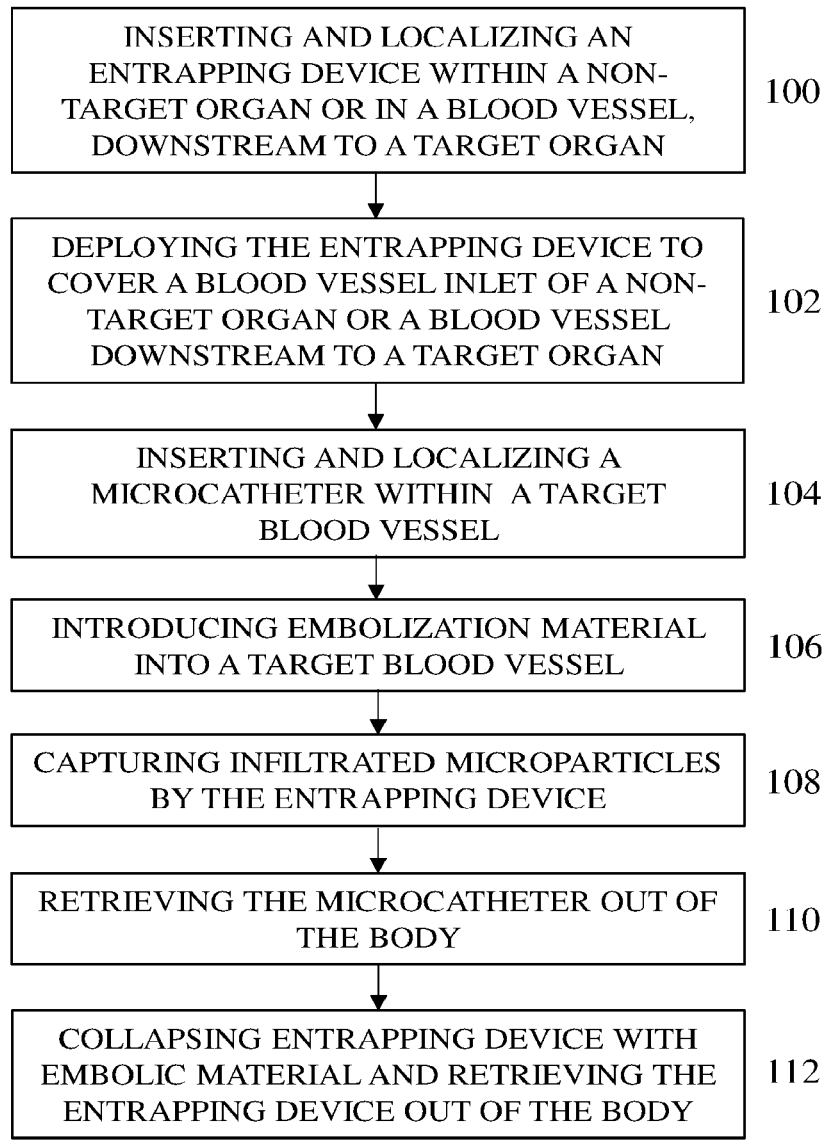
FIG. 1 is a flow diagram illustrating an exemplary method of performing an embolization therapy while preventing non-target deposition of embolic material in a non-target organ, in accordance with some embodiments of the present invention.

The present invention, in some embodiments thereof, relates to devices, methods and kits for preventing non-target microparticles deposition and embolization, in conjunction with delivering microparticles (e.g., an embolization material) via a blood vessel to a target bodily part. Some embodiments of the invention relate to devices and methods for entrapping infiltrated microparticles within the heart right atrium. Some embodiments of the invention are applicable for: (i) delivering embolization material in a small blood vessel towards a target bodily part, (ii) performing local embolization in a small blood vessel feeding a (possibly, cancerous) target bodily part, thereby forming emboli in small blood vessels; and (iii) capturing infiltrated microparticles within a non-target body organ or within a blood vessel, downstream to the target organ.

It is understood that the invention is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the invention. The following exemplary embodiments may be described in the context of exemplary embolization procedures for ease of description and understanding. However, the invention is not limited to the specifically described devices and methods, and may be adapted to various clinical applications without departing from the overall scope of the invention. It is also to be understood that the invention is not necessarily limited in its application to any particular sequential ordering of method steps or procedures, or to particular details of construction or/and arrangement of device or apparatus components set forth in the following illustrative description. The invention is capable of other embodiments or of being practiced or carried out in various ways.

Radioembolization is a common technique for treating hepatic neoplasms. Utilizing the dual hepatic blood supply, a therapeutic radiation dose, greater than 200 Gy may be delivered to tumors. Nevertheless, serious adverse effects caused by non-target deposition of radioactive microspheres are associated with current implementations of radioembolization. Non-target embolization and non-target deposition of radioactive microparticles within lungs are considered a main concern and are primarily associated with the creation of arteriovenous shunts that bypass the hepatic capillary bed and drain into the blood circulation. The phenomenon of increased pulmonary shunting is most frequently encountered in patients with advanced hepatocellular carcinoma. This type of patient population will commonly be prohibited from receiving treatment due to the high lung shunt fraction.

A further adverse effect associated with embolization therapy relates to retrograded flow (backflow or reflux) of the embolization material during injection thereof within a blood vessel. Embolic material backflow may infiltrate and accumulate within adjacent, upstream non-target organs or/and blood vessel, and cause serious complications.

Some embodiments of the present invention may provide a solution to phenomena of non-target deposition of embolic material or/and non-target embolization caused by either or both reflux and blood vessels shunting.

An aspect of some embodiments of the present invention relates to entrapping means or devices configured to entrap an embolic material (e.g., microparticles) and to methods for using same in preventing or minimizing non-target deposition of embolic material following an embolization therapy.

According to some embodiments, the present invention relates to microparticles entrapping means or devices and methods for using same in preventing or minimizing infiltration of embolization material from the liver to the lungs.

A further aspect of some embodiments of the invention relates to an embolization procedure with two layers of protection from non-target embolic material deposition that includes: i) positioning microparticles entrapping device within a non-target body organ or blood vessel; and ii) performing an embolization therapy with means applied to reduce reflux or backflow of the embolization material. This approach affords particularly safe embolization therapy aimed to prevent non-target deposition of microparticles caused by either or both the shunting and reflux phenomena.

In view of the above and as will be further described below, some embodiments of the present invention may provide a solution to the problem of non-target deposition of microparticles or/and non-target embolization, as well as providing kits, devices, and methods for performing techniques associated with microparticles administration, such as radioembolization, in an effort to improve therapeutic efficiency and safety.

Some embodiments of the invention concern the use of an embolic material entrapping device configured to be positioned before or within a non-target body organ or a blood vessel, downstream to a target body organ, with the use of a microcatheter that is configured to deliver microparticles, such as in a form of an infusion suspension.

The invention concerns, in some embodiments, the use of microparticles entrapping device configured to be positioned within the right atrium of the heart and a microcatheter configured to deliver a pharmaceutical composition or an infusion suspension, including microparticles and an infusion fluid.

According to some embodiments, the terms "pharmaceutical composition including microparticles" and "infusion suspension including microparticles" are used in conjunction and refer to an embolic material being provided within a carrier, excipient or an injectable infusion fluid.

As used herein, the terms "embolization material" and "embolic material" are used in conjunction and relate to materials, particles, or microparticles that can occlude a blood vessel. Embolization material, may present different forms, and may include, without limitation, beads, foam or glue. Embolization material, may be made from a material, including, but not limited to, a metal or/and a polymer, or/and a glass. Exemplary materials for producing embolization materials, include, without limitation polyvinyl alcohol (PVA), acrylamido polyvinyl alcohol, a hydrogel coated with Polyzene-F, two monomers that combine to form a copolymer (e.g., Ethylene vinyl alcohol copolymer (EVOH); Onyx), silicon dioxide ($SiO_2$), sodium oxide ($Na_2O$), sodium carbonate ($Na_2CO_3$), calcium oxide (CaO), silver, gold, palladium, platinum, tantalum (e.g. tantalum oxide), tungsten, iridium, titanium, magnesium, strontium, zinc, lanthanum, barium (e.g. barium sulfate), and stainless steel.

Optionally, certain substances may be added to the microparticles or the embolization materials, to enhance the therapeutic effect. Examples include, but are not limited to: pharmaceuticals (e.g., chemotherapeutics), and radioactive agents (e.g., ytrrium90).

As used herein the term "entrapping device" is interchangeable with the term "entrapping mean(s)" relates to means that entrap, capture or/and filter embolic material having a particular diameter within the range of 10 μm and 1,500 μm, 10 μm and 1,000 μm, 10 μm and 500 μm, 10 μm and 100 μm, 20 μm and 80 μm, or 20 μm and 60 μm. Each possibility represents a separate embodiment of the invention.

As used herein the term "preventing" refers to total preclusion, as well as to diminishing, minimizing, reducing, abolishing or abrogating non-target deposition of an embolic material. In some embodiments, non-target deposition of embolic material is completely abolished or prevented. In some embodiments, non-target deposition of embolic material is reduced by at least 10%, at least 20%, at least 30%, at least 40%, at least 50%, at least 60%, at least 70%, at least 80%, or at least 90%. Each possibility represents a separate embodiment of the invention.

As used herein the terms "target organ" or "target bodily organ" relates to any body organ or tissue that is chosen for treatment or/and is afflicted with a disease or condition that may be treated by therapy that includes an embolization therapy. The term specifically refers to body organs afflicted with a disease or condition that may benefit from an embolization therapy. Exemplary diseases include, without limitation, cancer, hemorrhage and arteriovenous malformation (AVM). Exemplary body organs include, without limitation, liver, kidney, uterus, brain, and prostate. In contrary, the terms "non-target organ" or "non-target bodily organ" will refer herein to organs that may be prone to embolic material infiltration due to the embolization therapy or/and which are chosen for particular protection by the medical practitioner.

In exemplary embodiments, entrapping, capturing or/and filtering may be temporary, optionally, until end of an embolization therapy procedure, until withdrawal of the microparticles entrapping device from the non-target body organ or blood vessel, or following a chosen time, after ceasing of delivering the embolic material. According to some embodiments, chosen time is sufficient for allowing the entrapping device to entrap infiltrating embolic material.

As used herein the term "chosen time" may be any time, following which the practitioner ceases delivering an embolic material. According to some embodiment, the chosen time is within the range of 1 minute to 20 minutes, 1 minute to 10 minutes, or 1 minute to 5 minutes. Each possibility represents a separate embodiment of the invention.

According to some embodiments, the invention is applicable for filtering or entrapping microparticles (e.g., of an embolic material) infiltrated, for example, towards or into the right atrium from any target organ, following treatment of the organ with embolic material. The entrapping device of the invention is most useful in capturing embolic material infiltrated to the blood circulation (i.e., the inferior vena cava or the superior vena cava) from an organ blood outflow, following an embolization procedure. Exemplary diseases that may be treated with an embolization therapy include, without limitation, cancer that has spread (metastasized) to the liver from a primary tumor elsewhere (e.g., colorectal cancer, breast cancer, lung cancer and neuroendocrine tumors), cancer originating in the liver (such as hepatocellular carcinoma and cholangiocarcinoma), renal tumors (benign and malignant), tumor within the uterine (e.g., uterine fibroid), a brain cancer (e.g. meningioma), a prostate cancer and a colorectal cancer.

An exemplary treatment site may include the liver, where deposition of embolic material and embolization may occur by embolization material infiltration to the lungs via arteriovenous shunts.

As used herein the term "a blood vessel, downstream to the target organ" is interchangeable with the term "non-target blood vessel" and refers to a vessel to which blood drains from a target body organ or a target body organ outflow blood vessel. A blood vessel, downstream to the target organ is selected from: an organ outflow blood vessel, an inlet of a non-target organ, or a junction of two or more organ outflow blood vessels.

An organ outflow blood vessel may, according to some embodiments, be a hepatic vein or an inferior vena cava. An inlet of a non-target organ may, according to some embodiments, be an inlet opening of the right atrium. A junction of two or more organ outflow blood vessels may, according to some embodiments, be a junction between an inferior vena cava and a hepatic vein.

Reference is now made to FIG. 1 of a flow diagram illustrating an exemplary method of performing an embolization therapy while preventing non-target deposition of embolic material in a non-target organ. As shown in FIG. 1, in a non-limiting manner, and in some embodiments, the method includes the following exemplary steps (procedures/processes).

At exemplary step 100, an entrapping device (for example, as illustratively described below) is inserted and localized within a non-target organ or in a blood vessel, downstream to a target organ. At exemplary step 102, there is expanding or deploying the entrapping device or/and a filter included therein to an expanded configuration. At exemplary step 104, a microcatheter, for delivering embolization material, is inserted into a blood vessel feeding a target bodily organ. At exemplary step 106, a suspension including microparticles is injected via the microcatheter towards the body organ via the blood vessel to thereby facilitate a blood vessel occlusion. In exemplary embodiments, each or both steps 100 and 102 may occur in conjunction with (prior, concomitantly or after) each or both steps 104 and 106. At exemplary step 108, microparticles, if infiltrated from the treated (target) body organ to the blood circulation feeding the heart, are then filtered, collected, or/and captured by the entrapping device, optionally in a pocket formed with the filter.

Upon completion of at least one of: infusing the embolization material to the body organ (step 106), and retrieval of the microcatheter from the blood vessel out of the body (step 110), the entrapping device is collapsed and withdrawn back into the delivery sheath or/and catheter and removed from the body organ or blood vessel, downstream to a target organ, together with the captured embolic debris (step 112).

Additional details and features of the method of performing an embolization therapy while preventing non-target deposition of embolic material in a non-target organ, are provided hereinbelow following description of exemplary embodiments of an embolic material (e.g., particles) entrapping device.

According to an aspect of the invention, there is provided an entrapping device for entrapping an embolic material infiltrated to blood flow following delivery thereof into a blood vessel feeding a target organ, the entrapping device includes a filter configured for filtering and entrapping the embolic material.

According to some embodiments, the entrapping device may be positioned within a non-target body organ or blood vessels. The entrapping device may be positioned to cover an inlet opening of the right atrium. As used herein the term "inlet opening of the right atrium" may be one of: i) the position where the inferior vena cava enters the right atrium; and ii) the position where the superior vena cava enters the right atrium. In accordance with those embodiments, the entrapping device is configured to cover such inlet opening of the RA.

According to some embodiments, the entrapping device may be used, positioned and deployed within a blood vessel, downstream to the target organ.

FIGS. 2A-2H shows an entrapping device 300 which includes a filter 308, and a filter collapsing mechanism 305 sized for positioning in a catheter lumen of a filter delivering catheter 304. Filter collapsing mechanism 305 is actuatable with a proximal end thereof from outside the subject body. According to some embodiments, entrapping device 300 may be used, positioned and deployed within the non-target body organ or in a non-target vessel using a suitable delivery system.

The delivery system may include at least one of: filter delivery catheter 304, a delivery sheath 302, and a guidewire 306. The delivery sheath 302 and catheter 304 may include a proximal end, a distal end and a lumen extending therebetween the ends and opened at proximal and distal ends. The guidewire 306 may be in the form of a cord. According to some embodiments, at least one of delivery sheath 302 and catheter 304 is configured to house entrapping device 300 when in a compressed or/and collapsed configuration.

According to some embodiments, the filter collapsing mechanism 305 includes an elongated body 314 configured for slideably passaging through and beyond a longitudinal axis of the delivery sheath 302 or catheter 304. Elongated body 314 may be rod or a tube and may be distally attached to filter 308. According to some embodiments, the guidewire 306 facilitates access and delivery of the delivery sheath 302 or/and catheter 304 towards and into the right atrium or the vena cava or any other non-target blood vessel or body organ.

According to some embodiments, the filter delivery catheter 304 is about 3 mm or less in outer diameter, optionally 0.5 mm to 2 mm. According to some embodiments, the catheter is about 150 cm long.

According to some embodiments, the entrapping device 300 is collapsible. According to some embodiments, the entrapping device is compressed within the delivery sheath 302 and catheter 304 using the elongated body. In accordance with this embodiment, the entrapping device 300 has compressible or/and collapsible or/and self-expandable geometry. According to some embodiments, the entrapping device 300 is elastic and flexible generally along and about a central longitudinal axis of the catheter. According to some embodiments, the entrapping device 300 is automatically deployable to seal a non-target body organ or blood vessel (e.g., an interior wall or opening of the right atrium). According to some embodiments, the entrapping device is configured for intimate contact with the non-target body organ or blood vessel (e.g., an interior wall or opening of the right atrium), for the primary purposes of filtration of embolization material, but allows the passage of blood therethrough.

According to some embodiments, filter collapsing mechanism 305 further includes a circumferential hollow sleeve 310 proximally attached to an opened perimeter of the filter 308. According to some embodiments, the sleeve 310 may include a drawstring 312 for use in forcibly collapsing, or elongating, or reducing the shape and profile of the filter subsequent to deployment and use thereof.

According to some embodiments, when unrestrained, the filter 308 normally returns to its original unstressed shape. According to some embodiments, the device is suitable for self-expansion of the filter 308 when emerging from within a catheter 304 or delivery sheath 302.

According to some embodiments, filter 308 is configured for expanding, and additionally configured for collapsing in response to conformation thereof to outside boundaries of different sizes.

According to some embodiments, filter 308 includes one or more mesh or woven filtration layers. According to some embodiments, the filter includes a fine mesh having strands with a thickness of no more than 200 micrometers, 150 micrometers, 100 micrometers, 50 micrometers, 25 micrometers, 10 micrometers, or 5 micrometers. Each possibility represents a separate embodiment of the invention. According to some embodiments, the filter 308 including pores configured to entrap embolic material having a diameter that equals to or above a predetermined size. According to some embodiments, the predetermined size is 20 micrometers or above or 30 micrometers above. Each possibility represents a separate embodiment of the invention.

According to some embodiments, the shape of the filter 308 exhibits a half circle, a cone, a cap shape, or a bowl shape. According to some embodiments, the filter 308 is opened to an umbrella or a parachute like shape. According to some embodiments, the maximal diameter of the filter 308 when is in the open configuration is 10 mm to 50 mm. According to some embodiments, the filter includes pores with a pore size of about 500 micrometers or less, about 400 micrometers or less, about 300 micrometers or less, about 200 micrometers or less, about 100 micrometers or less, about 80 micrometers or less, about 70 micrometers or less, about 60 micrometers or less, about 50 micrometers or less, about 45 micrometers or less, about 40 micrometers or less, about 35 micrometers or less, or about 30 micrometers or less or about 25 micrometers or less. Each possibility represents a separate embodiment of the invention. According to some embodiments, the filter 308 includes pores with a pore size between the range of 10 micrometers and 500 micrometers, 10 micrometers and 400 micrometers, 10 micrometers and 300 micrometers, 10 micrometers and 200 micrometers, 10 micrometers and 100 micrometers, 15 micrometers and 80 micrometers, 15 micrometers and 60 micrometers, 15 micrometers and 50 micrometers, 15 micrometers and 40 micrometers, or 15 micrometers and 30 micrometers. Each possibility represents a separate embodiment of the invention.

The filter may be formed of a polymeric material including, but not limited to polypropylene (PP), polyvinylchloride (PVC), polyamide (nylon), polyurethane, polyester, polyethylene terephalate, polyether-ether ketone (PEEK), polyether block amide (PEBA), polytetraflouroethylene (PTFE), or any mixture, blend or combination thereof. Alternatively, or additionally, the filter may be formed from a metal or metal alloy including, but not limited to stainless steel, nickel-titanium alloy (Nitinol), platinum or cobalt chrome.

Reference is again made to FIG. 1 of a flow diagram illustrating an exemplary method of performing an embolization therapy while preventing non-target deposition of embolic material in a non-target organ.

The method includes exemplary step 100, in which the herein disclosed entrapping device is inserted and localized within a non-target organ (e.g., in the right atrium) or in a blood vessel, downstream to a target organ (e.g., within the inferior vena cava, above the hepatic veins or at a junction between the inferior vena cava and the hepatic vein). According to exemplary embodiments, the entrapping device is inserted to and localized at the RA. In accordance with those embodiments, the entrapping device may be inserted and localized within the RA when provided with catheter delivery system being introduced to the jugular vein and then to the superior vena cava and thereafter localized within the RA. Alternatively, the entrapping device may be introduced to the RA, when provided within a delivery system that is firstly introduced to the femoral vein, and then to the inferior vena cava and thereafter localized within the RA. As will be explained in more details below, delivery system may include at least one of: a delivery sheath, a guidewire and a catheter for guiding and facilitating safe and efficient delivery of the entrapping device at the non-target organ or in a blood vessel, downstream to a target organ. Optionally, or additionally a delivery of contrast enhancement material is injected within a blood vessel through which the catheter should be introduced, for example, in order to verify correct anatomy and positioning. The catheter thereafter follows the guidewire path within the body until localizing at the appropriate position.

The method further includes exemplary step 102 of expanding or deploying the entrapping device or/and a filter included therein to an expanded configuration. The entrapping device may be deployed after retracting the catheter proximally to reveal the entrapping device, or may be pushed distally out of the catheter. The entrapping device or/and the filter is thus automatically or self-deployed in outwardly directed expansion. Such expansion causes contact of the filter with a non-target organ blood vessel inlet or a wall of a blood vessel, downstream to a target organ. When the entrapping device is to be employed within the RA, the filter is positioned to cover an inlet of the right atrium through the interior of the right atrium. The RA inlet may be an inlet of the superior vena cava or of the inferior vena cava. When the filter is in the open configuration, the entrapping device is incorporated in a general filtration process, whereby embolization materials may be collected if flowing towards or/and into the RA after infiltrating from target organ.

The method further includes exemplary step 104 whereupon a microcatheter, for delivering embolization material, is inserted into a blood vessel feeding a target bodily organ. Optionally, or additionally, a delivery of contrast enhancing material is injected in the target blood vessel in order to verify correct anatomy and positioning. According to some embodiments, and when a blood vessel feeding the liver is to be treated, the microcatheter is inserted in the femoral artery and through the hepatic artery to a target blood vessel.

At exemplary step 106, a suspension including microparticles is injected via the microcatheter towards the body organ via the blood vessel to thereby facilitate a blood vessel occlusion. It is to be noted that each or both steps 100 and 102 may occur in conjunction with (prior, concomitantly or after) each or both steps 104 and 106.

At exemplary step 108, microparticles, if infiltrated from the treated (target) body organ to the blood circulation feeding the heart are then filtered, collected, or/and captured by the entrapping device, optionally in a pocket formed with the filter.

Upon completion of at least one of: infusing the embolization material to the body organ (step 106), and retrieval of the microcatheter from the blood vessel out of the body (step 110), the entrapping device is collapsed and withdrawn back into the delivery sheath or/and catheter and removed from the body organ or blood vessel, downstream to a target organ, together with the captured embolic debris (step 112). Device collapsing is made over the entire amount of entrapped microparticles, and is performed either selectively outside delivery sheath or/and lumen or by forcing it into the delivery sheath or/and lumen. In accordance with this embodiment, the entrapping device is reshaped to the original configuration following trapping the embolization material. It is to be noted that step 110 may be conducted after, concomitantly with or before step 112.

Reference is now made to FIGS. 2A-2H which show schematic side cut views representing possible scenarios of implementing exemplary embodiments of a method for applying entrapping means within a right atrium for preventing non-target embolization or/and deposition of an embolization material. The figures present the use of an entrapping device 300, and a delivery system including at least one of: a delivery sheath 302, a catheter 304, and a guidewire 306. The entrapping device 300 includes a filter 308 for entrapping microparticles above a predetermined size, while allowing blood flow to pass therethrough. The entrapping device may further include a circumferential hollow sleeve 310 attached to an opened perimeter of filter 308. Circumferential hollow sleeve 310 is configured for housing at least one drawstring 312, configured for facilitating at least one of: deployment, closure, or collapsing of the entrapping device 300.

Optionally, additionally or alternatively, the entrapping device 300 includes an elongated member 314 distally attached to filter 308 or to circumferential hollow sleeve 310. Elongated member 314 is configured to house within an inner lumen thereof, drawstring 312. The entrapping device 300 is self-deployed, following proximal retrieval of the catheter 304 or/and the delivery sheath 302, or/and following distal pushing elongated member 314 out of the catheter 304 or/and delivery sheath 302, to employ expansion and localization thereof within an inlet opening of the RA.

Figure 2A:
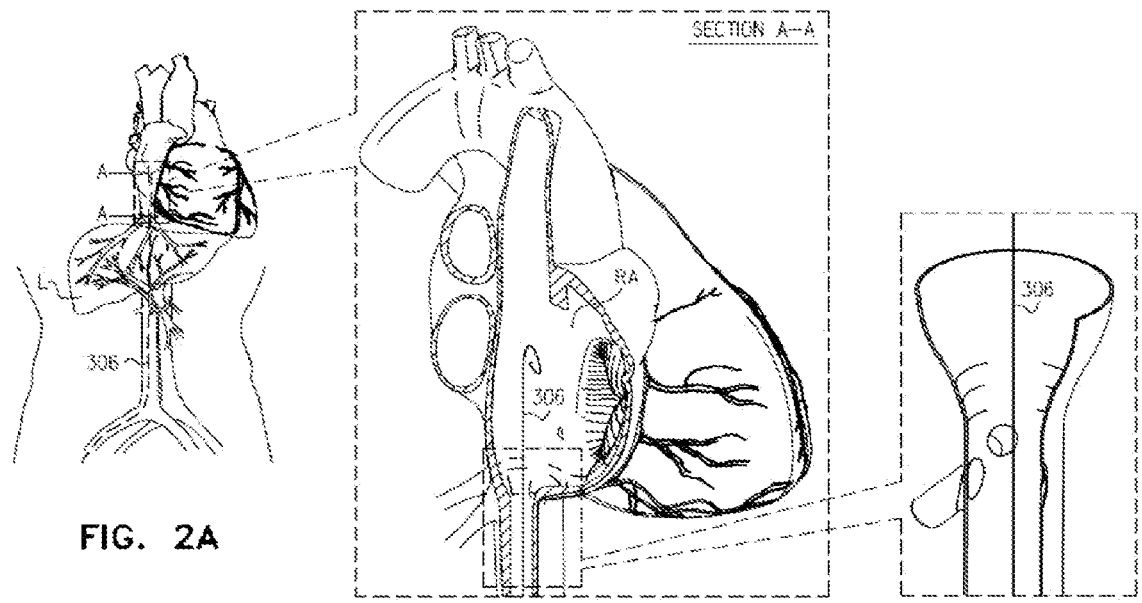
FIGS. 2A-2H are schematic side cut views representing possible scenarios of implementing exemplary embodiments of a method for applying an entrapping device within a right atrium, in accordance with some embodiments of the invention.
Figure 2B:
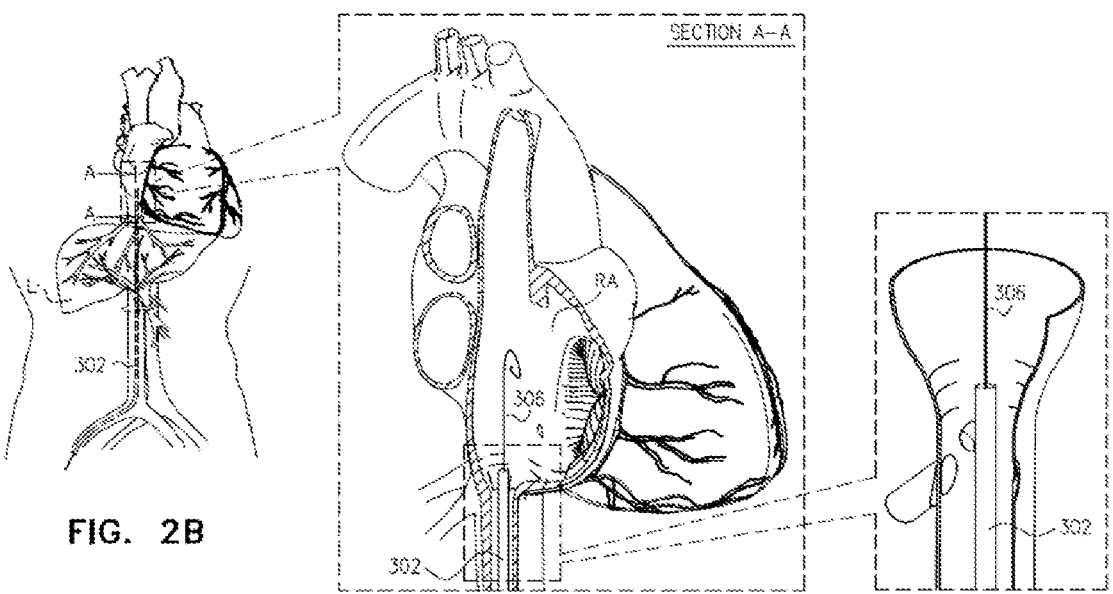
Figure 2C:
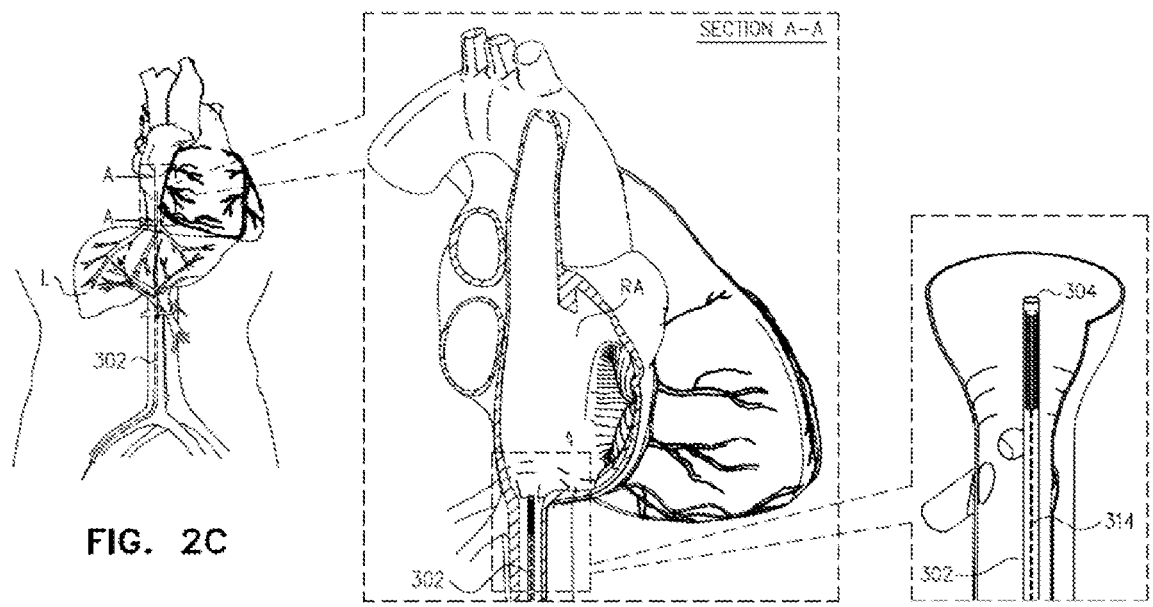
Figure 2D:
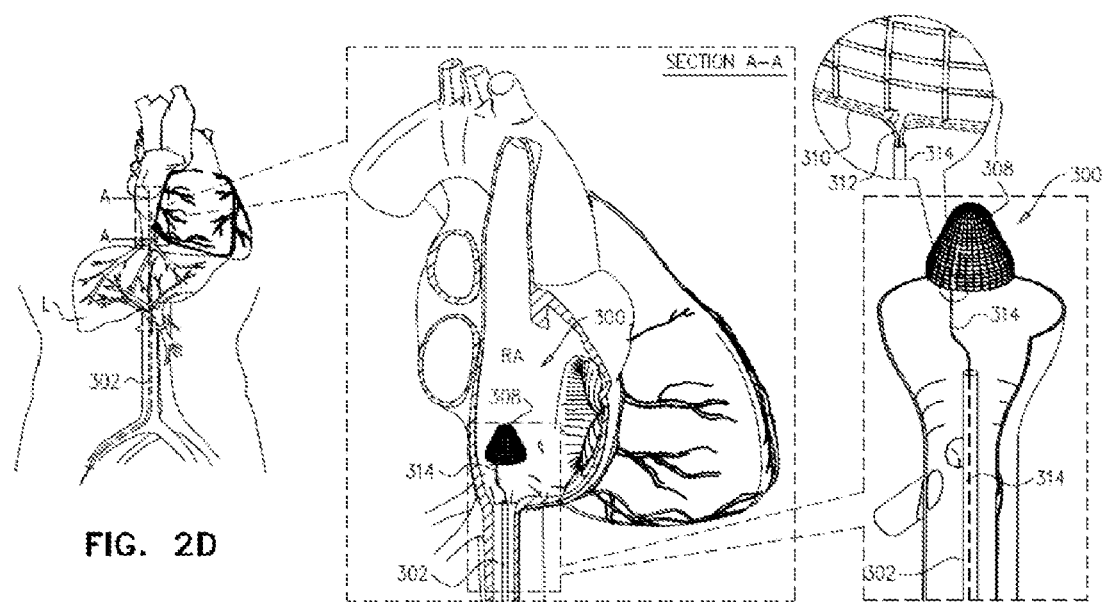
Figure 2E:
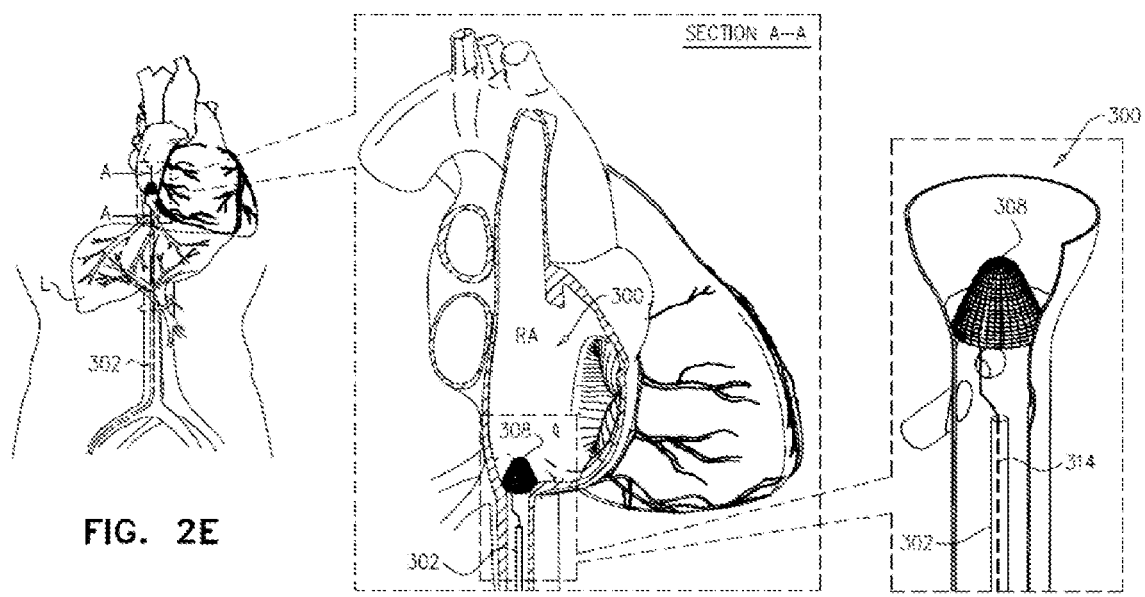

The entrapping device 300 is sized and shaped to adapt an umbrella, a parachute-like structure, a cap shape or a cone shape. FIG. 2A shows a step of positioning distal end of a guidewire 306 within a right atrium RA in a heart, before applying targeted embolization treatment to a liver. FIG. 2B shows a step of positioning a distal opening of a delivery sheath 302 in right atrium RA following passing thereof over guidewire 306. Guidewire 306 may then be withdrawn leaving delivery sheath 302 in-place. Catheter 304 may then be introduced within a lumen of delivery sheath 302, and delivery sheath 302 may stay in place or be withdrawn, leaving catheter 304 in place (shown in FIG. 1C).

Figure 2F:
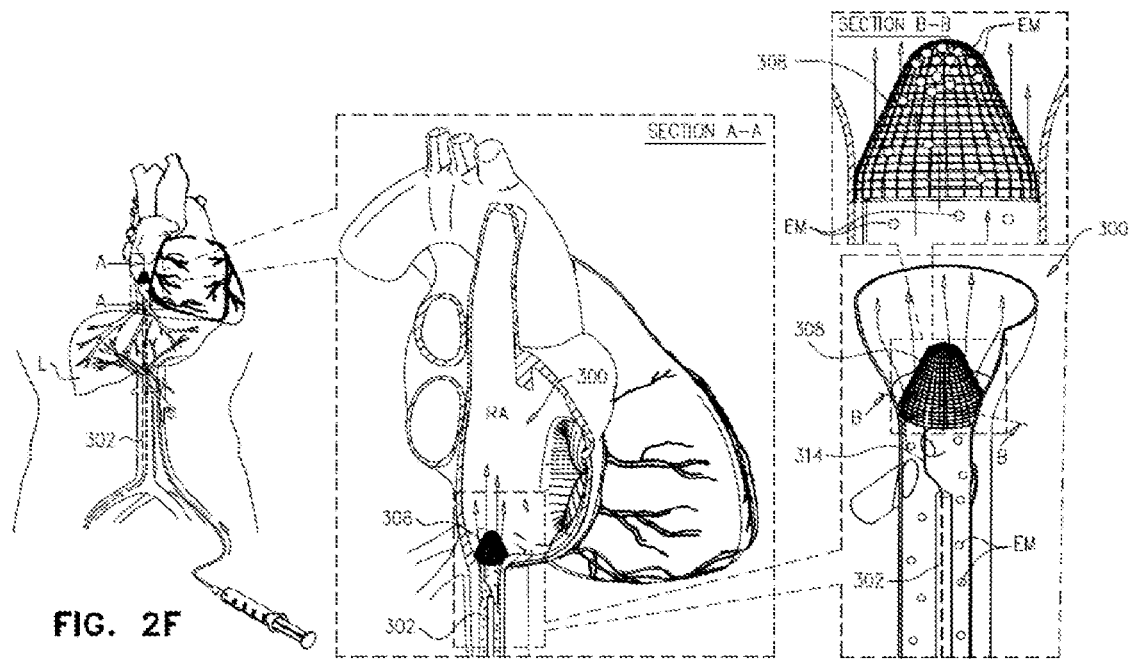
Figure 2G:
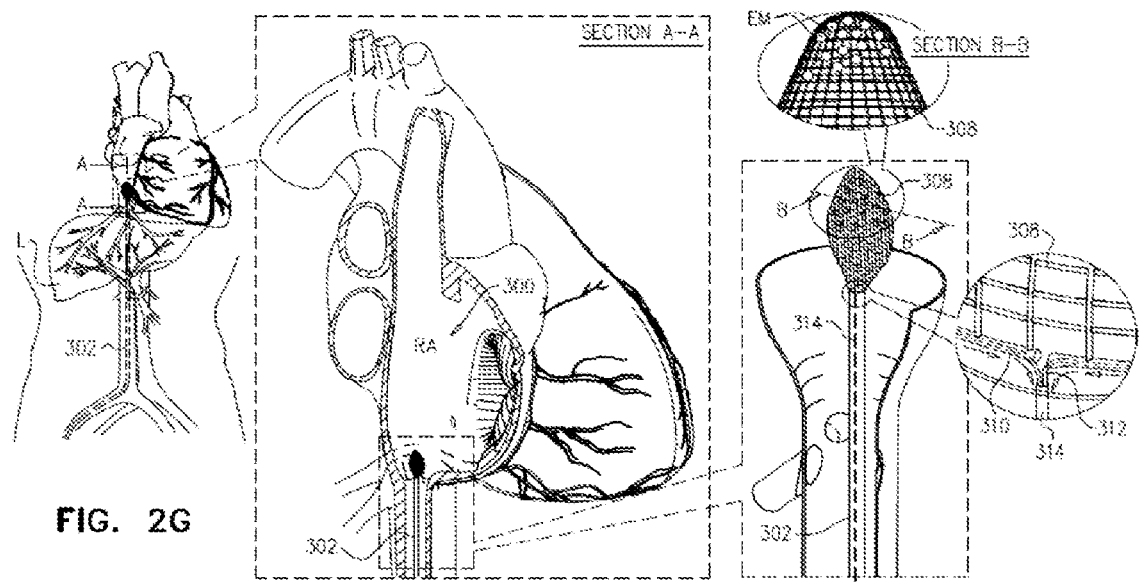

Alternatively, entrapping device 300 may be independently inserted within delivery sheath 302 (not shown). FIG. 1D shows a result of retrieval of the catheter 304 or/and the delivery sheath 302, or/and distal pushing elongated body 314 through lumen and distal opening of catheter 304 or/and delivery sheath 302 into right atrium RA, whereby entrapping device 300 self-expands. FIG. 1E shows a step of deploying entrapping device 300 above right atrium inlet opening, covering it entirely, so that no embolization bead above a predetermined threshold size could infiltrate through (in accordance with mesh opening size). In some embodiments, embolization treatment in the liver may begin once entrapping device 300 is deployed, optionally using any of the microcatheters or/and any of the methodologies described herein. FIG. 2F shows filtering or entrapping infiltrated embolization material EM within the RA with entrapping device 300. FIG. 1G shows filter 308 enclosure over entrapped embolic material EM, by proximal pulling drawstring 312, thereby forming a pocket within which EM is entrapped. Following closure of filter 308 over microparticles, the entrapping device 300 is forcibly withdrawn and re-collapsed back into lumen of catheter 304 or/and delivery sheath 302 by proximally pulling, backward elongated member 314 or/and drawstring 312.

Figure 2H:
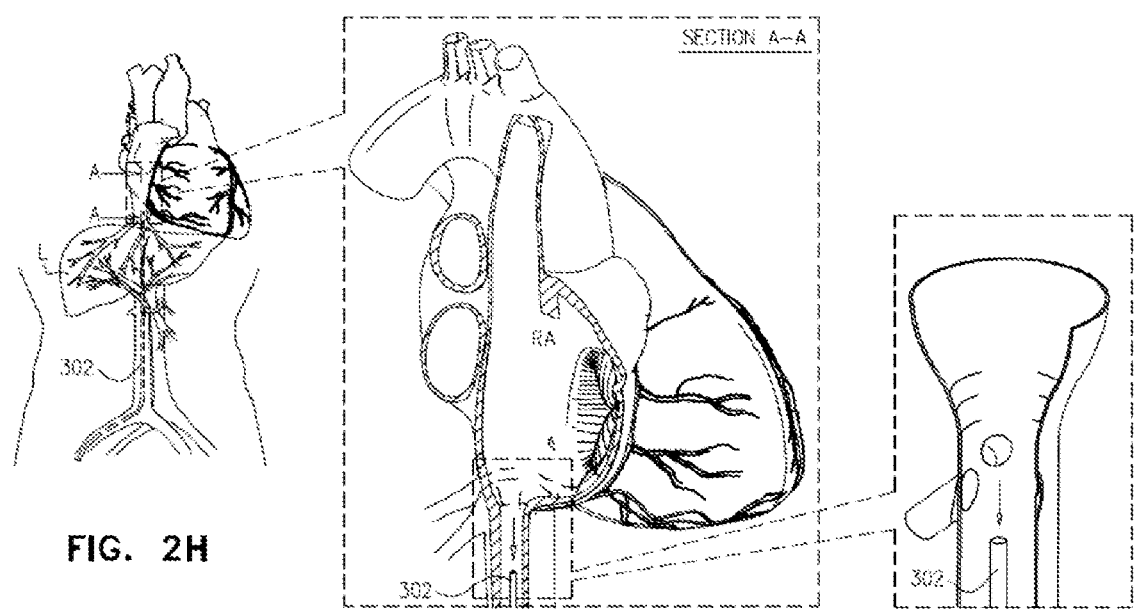

FIG. 2H shows withdrawal of the catheter 304 or/and delivery sheath 302 with entrapping device 300 from right atrium RA.

According to an aspect of the invention, there is provided a method for delivering particles in a blood vessel feeding a target organ in a body of a subject, the method including at least one of the following steps (not necessarily in same order):

positioning an entrapping device in a blood vessel, downstream to the target organ, the entrapping device is configured to filter embolic material from blood flow, and to entrap the embolic material;

placing a distal outlet of a catheter in the blood vessel feeding the target organ;

delivering the embolic material via the distal outlet in the blood vessel towards the target organ;

applying a flow disturbance mechanism in the blood vessel, proximally to the distal outlet, for creating a local disturbance in blood flow thereby suppressing a retrograded flow of the particles flowable in a proximal direction; and removing the entrapping device from subject body following a chosen time after ceasing of the delivering, sufficient for allowing the entrapping device to entrap infiltrating embolic material infiltratable in a blood vessel, downstream to the target organ.

Figure 3A:
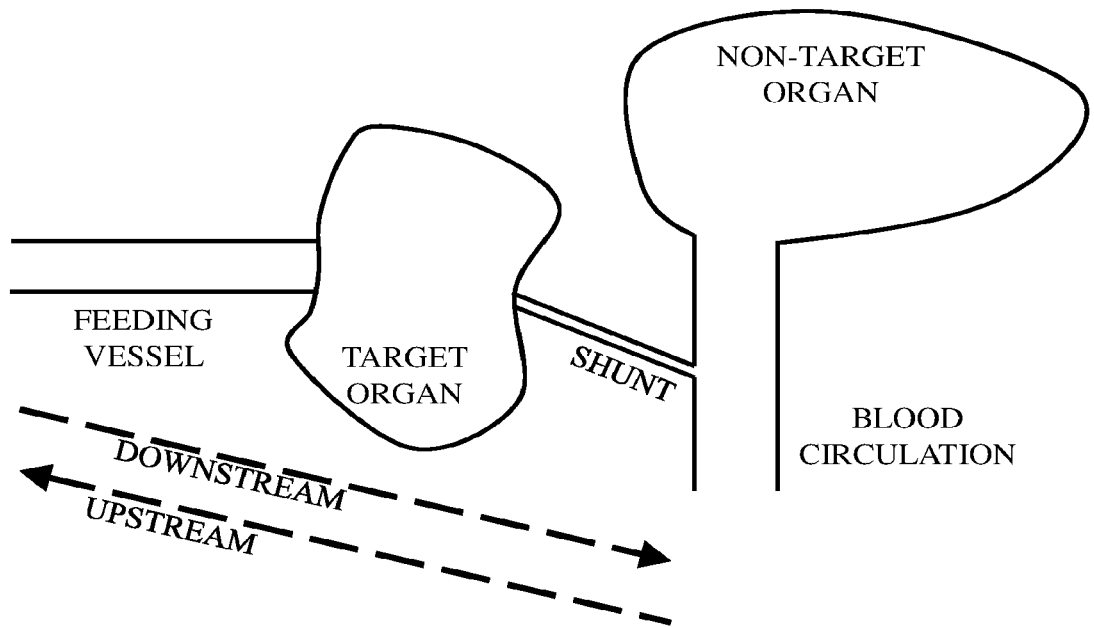
FIGS. 3A-3G are schematic illustrations showing a microcatheter for delivering embolic material within a blood vessel of a target organ provided with means for disturbing a retrograded flow, and an entrapping device for filtering and entrapping microparticles, infiltrated from the delivered embolic material, deployed from within a non-target organ, in accordance with some embodiments of the invention.

According to another aspect of the invention, there is provided a method of applying a multi-layered protection from non-target embolization or/and non-target deposition of microparticles in a body of a subject, the method including at least one of the following steps (not necessarily in same order):

positioning an entrapping device in a first anatomical location downstream to a target organ, the entrapping device is configured to filter the microparticles from blood flow and to entrap the microparticles;

placing a distal outlet of a microcatheter in a second anatomical location upstream to the target organ;

delivering an infusion suspension including the microparticles via the distal outlet in the second anatomical location upstream to, and towards, the target organ;

by allowing a continuous blood flow downstream towards the target organ and away from the target organ, applying a flow disturbance mechanism in the second anatomical location, proximally to the distal outlet, thereby creating a local disturbance in blood flow for suppressing a retrograded flow of the microparticles flowable upstream to the target organ; and removing the entrapping device from the subject body following a chosen time, after ceasing of the delivering, sufficient for allowing the entrapping device to entrap infiltrating microparticles infiltratable upstream through the flow disturbance mechanism or/and downstream to the target organ. FIGS. 3A-3G and FIGS. 4A-4G are schematic illustrations showing possible sequential steps of employing the methods of the invention, and in particular, a method of applying a multi-layered protection from non-target embolization or/and non-target deposition of microparticles in a body of a subject. The embodiments described in FIGS. 3A—3G are provided with reference to an entrapping device 350 which is similar or identical in design and configurations to the previously disclosed entrapping device 300, and is configured to filter microparticles from blood flow and to entrap these microparticles. FIGS. 3A and 4A schematically illustrate "downstream" and "upstream" blood flow in accordance with the embodiments of the invention. As used herein the term "downstream" refers to the accommodation of general/normal blood flow direction, and in some occasions from a "target organ" to a "non-target organ", and the term "upstream" refers to a direction against the blood flow. In a particular example, "downstream" in an artery corresponds to normal flowing direction of oxygenated blood generally towards an organ receiving oxygen, while "upstream" in same artery means against this natural flow (i.e. in case of abnormal retrograde flow). In presence of abnormal shunts directly connecting arterial system with a vein (such as in the case of shunts connecting liver blood vessels to vena cava), "downstream" can also refer to the direction from the "target organ" towards a "non-target organ", in a blood flow therebetween, and "upstream" shall mean the opposite from that. The FIGs. further illustrates "a target organ", being an organ to which embolization therapy should be applied to and the term "non-target organ", being any other organ amenable to non-target deposition of embolic material.

Figure 3B:
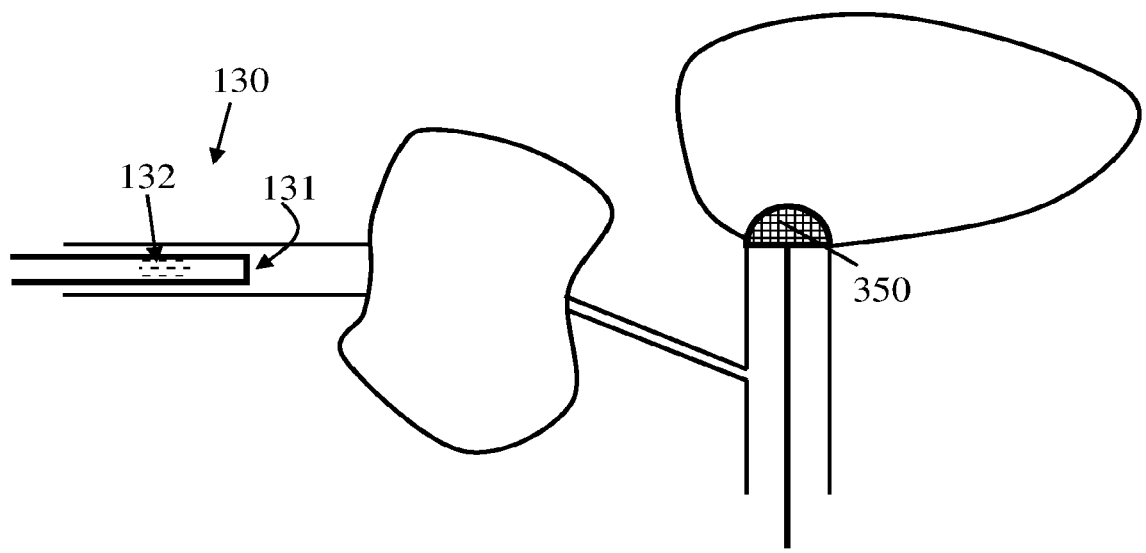
Figure 3C:
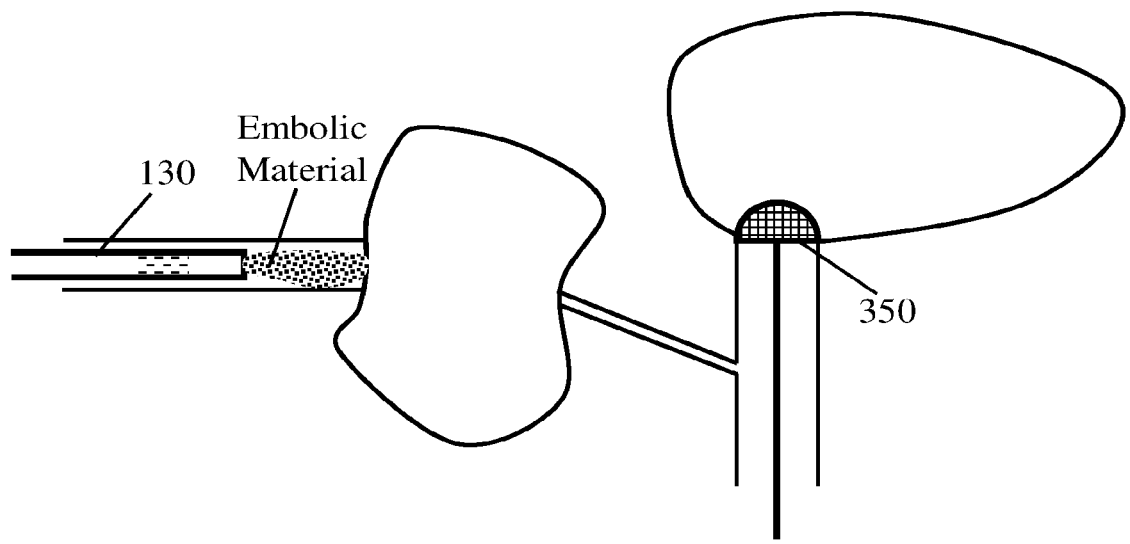
Figure 3D:
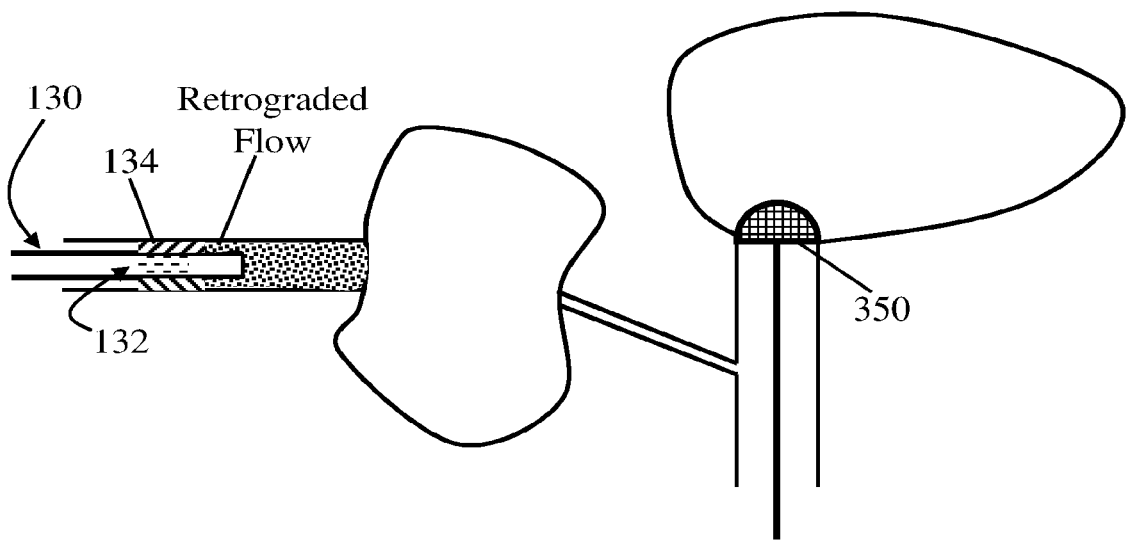
Figure 3E:
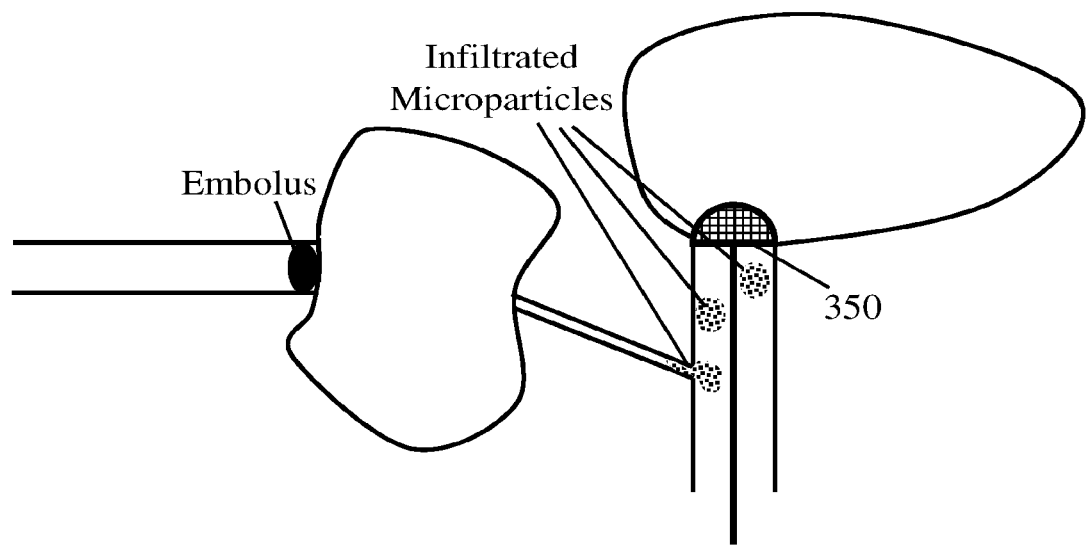
Figure 3F:
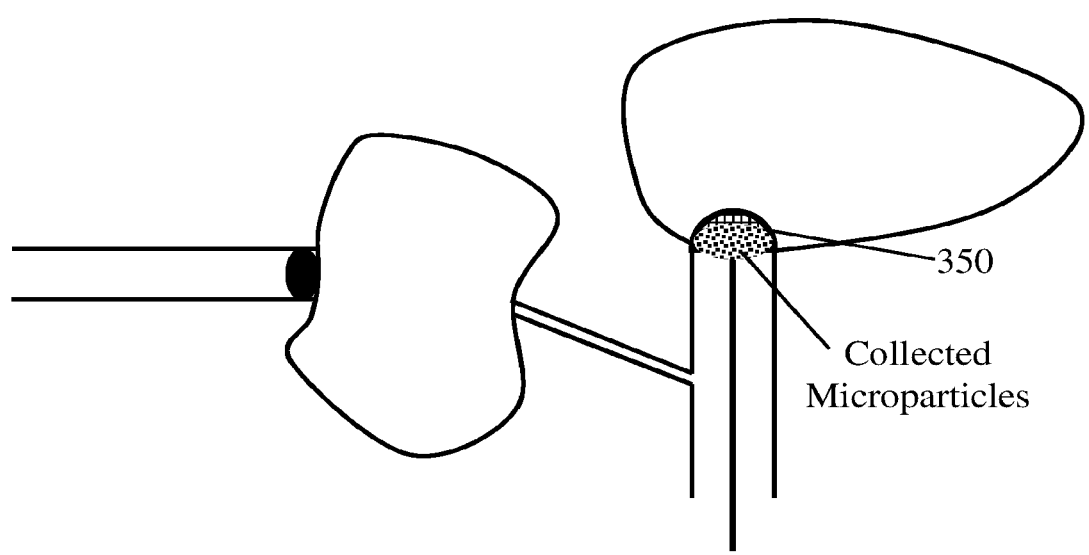
Figure 3G:
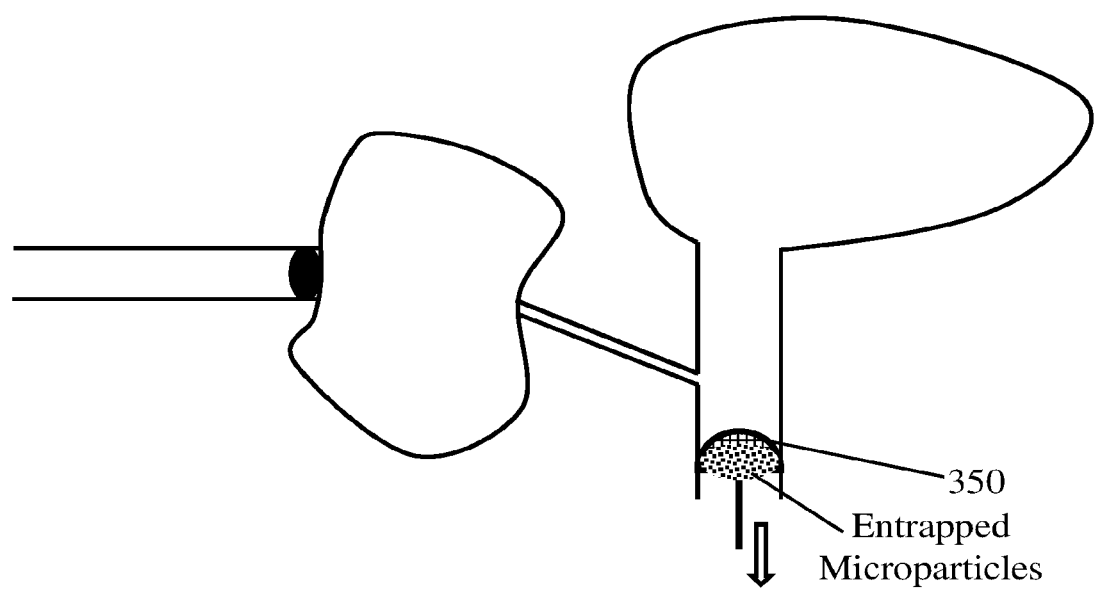
Figure 4A:
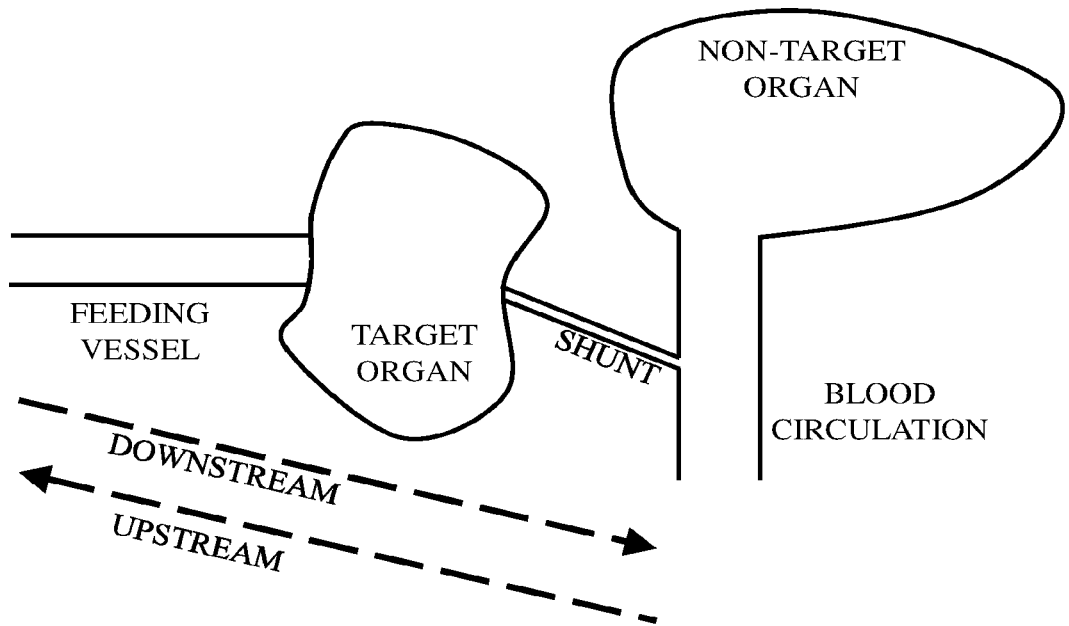
FIGS. 4A-4G are schematic illustrations showing a microcatheter for delivering embolic material within a blood vessel of a target organ provided with means for disturbing a retrograded flow, and an entrapping device for filtering and entrapping microparticles, infiltrated from the delivered embolic material, deployed at a non-target vessel downstream to a target organ, in accordance with some embodiments of the invention.
Figure 4B:
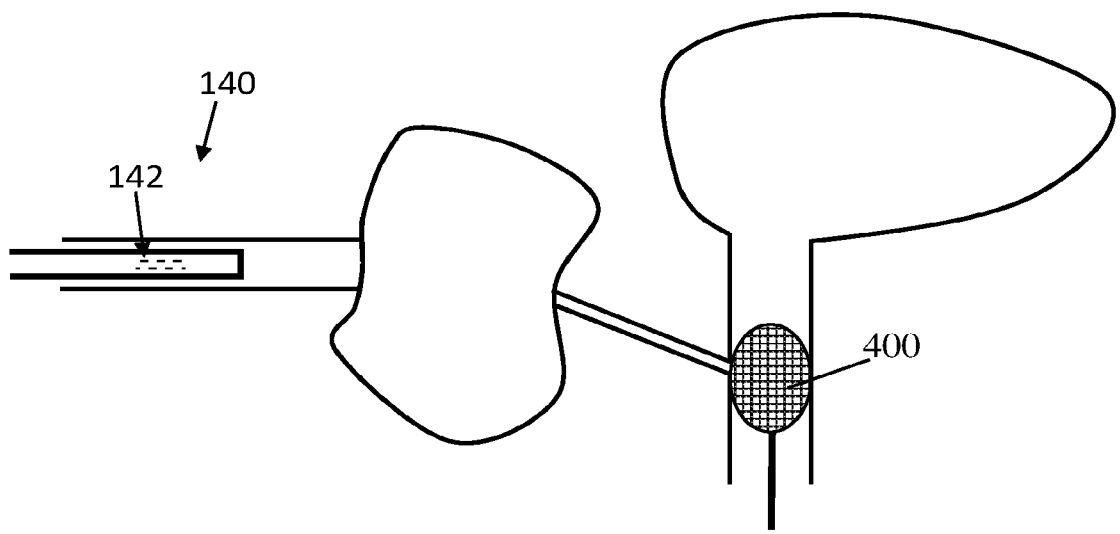
Figure 4C:
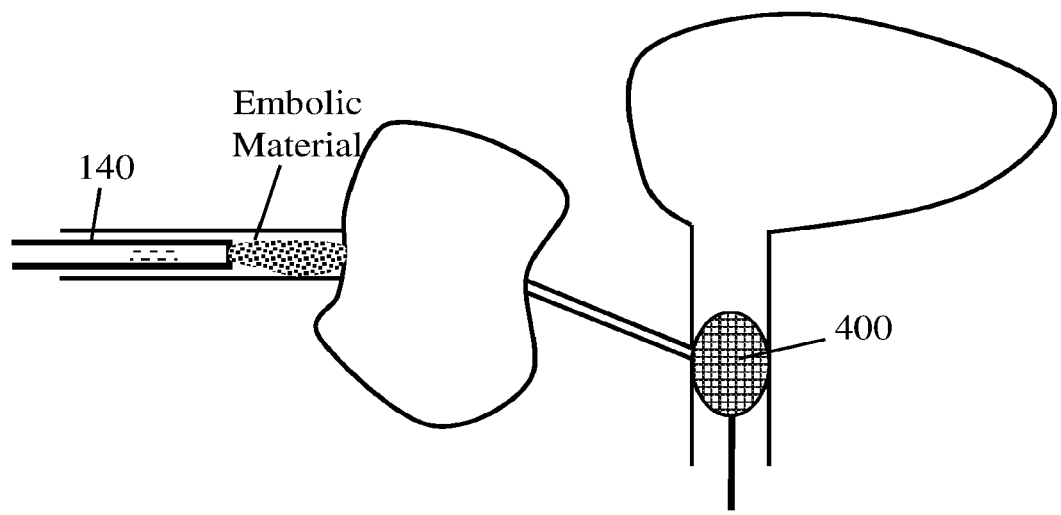
Figure 4D:
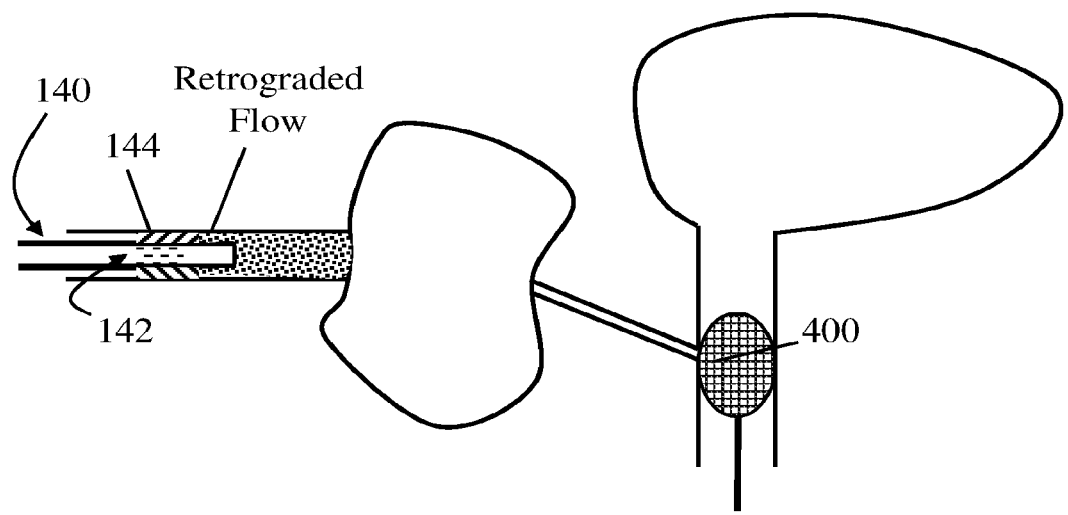
Figure 4E:
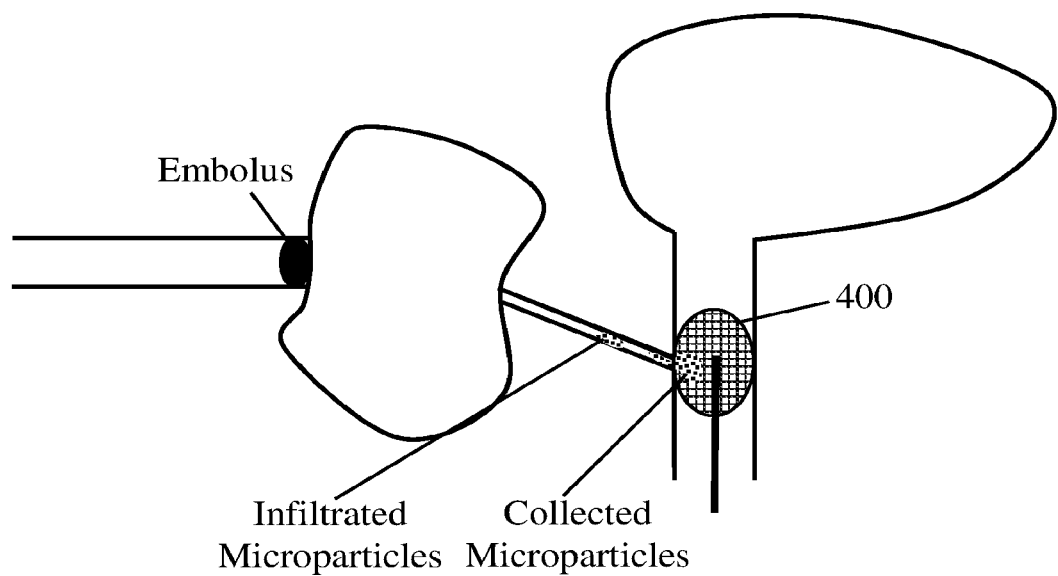
Figure 4F:
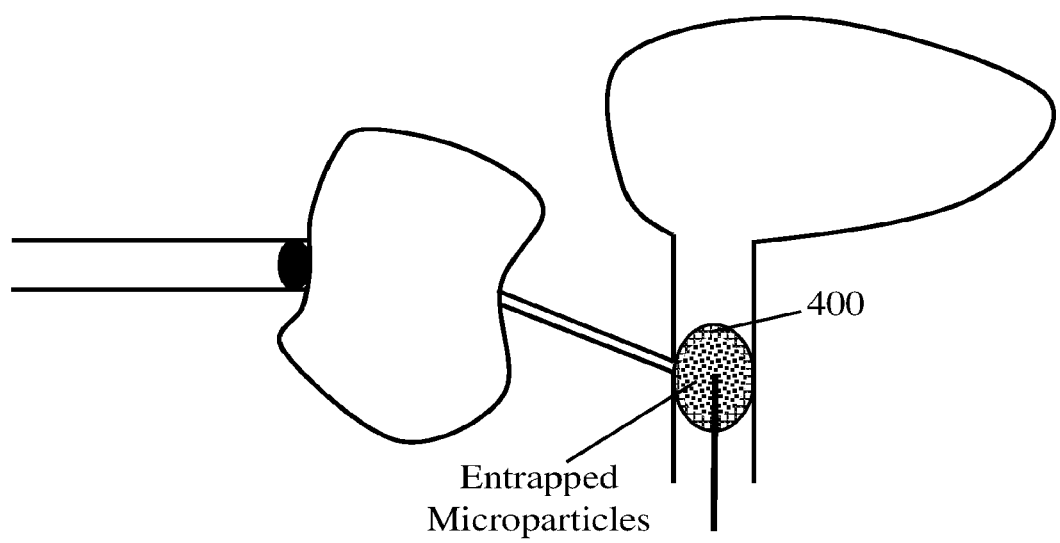
Figure 4G:
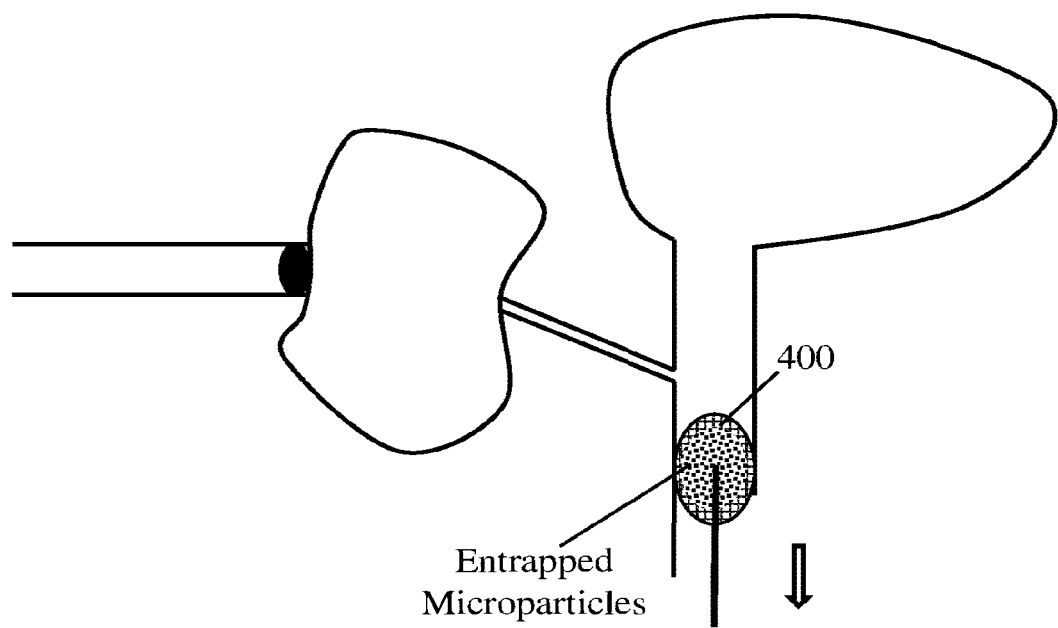

FIG. 3B shows: (a) positioning entrapping device 350 in a first anatomical location (in this example, the right atrium) downstream to a target organ (in this example, a liver), in conjunction (before, during or/and after) with (b) placing a distal outlet 131 of a microcatheter 130 in a second anatomic location (in this example, a (blood) feeding vessel, located upstream to a target organ). Entrapping device 350 has a cap-like shape, as shown when expanded within the non-target organ (heart, right atrium), downstream of the target organ. FIG. 4B shows introduction of a microcatheter 140 within a blood vessel, upstream to a target organ and an entrapping device 400 within a blood vessel, downstream to the target organ. According to some embodiments, and as will be explained hereinbelow, each of microcatheters 130 and 140 includes a flow disturbance mechanism in a form of side openings (132 and 142, respectively), which is configured to reduce or prevent reflux (backflow) by creating a local disturbance in blood flow thereby suppressing a retrograded flow of embolic material flowable in a proximal direction. FIGS. 3C and 4C show introduction of embolic material via microcatheters 130 and 140 (respectively) into a blood vessel feeding the target organ. FIGS. 3D and 4D present blood flow disturbance (134 and 144, respectively) caused by fluid flowing out of side openings 104 of microcatheter 100, in view of emerging of a retrograded flow of the microparticles. FIGS. 3E and 4E show emboli within a blood vessel feeding a target organ following embolization procedure and embolic material infiltrated via blood vessel shunts. FIGS. 3F and 4F show entrapping of infiltrated embolic material within a non-target organ (FIG. 3F) or within a blood vessel, downstream to a target organ (FIG. 4F). The entrapping device 300 with the entrapped embolic material is then withdrawn from the body (FIGS. 3H and 4H).

As detailed and describes herein the method of the invention assumes the use of a microcatheter for delivering an embolization material.

According to some embodiments, the microcatheter used is configured to reduce or minimize non-target microparticles deposition caused by reflux or backflow, of the embolization material or by shunts.

According to some embodiments, the microcatheter includes: a tubular wall including a proximal wall end, a distal wall end, and a lumen extending between the wall ends, the lumen is opened to a distal outlet at the distal wall end and to a plurality of side openings distributed around or/and along a section of the tubular wall proximally to the distal outlet;

the embolization microcatheter is configured to deliver an infusion suspension of particles in an infusion fluid, via the lumen to the distal outlet;

wherein the distal outlet is shaped or/and sized to allow passage there through of the infusion suspension of the infusion fluid and the particles, and each the side opening is shaped or/and sized to allow passage there through of the infusion fluid and to block passage there through of the particles.

Figure 5A:
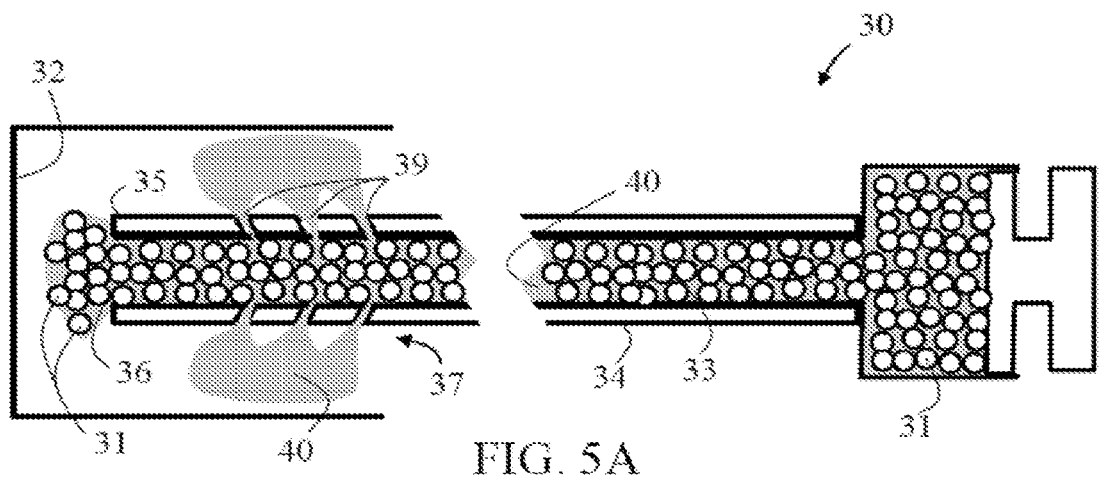
FIGS. 5A-5B are schematic side cut views of exemplary embodiments of a microcatheter during delivery of an embolic material before (FIG. 5A) and after (FIG. 5B) occurrence of a retrograded flow, in accordance with some embodiments of the invention.
Figure 5B:
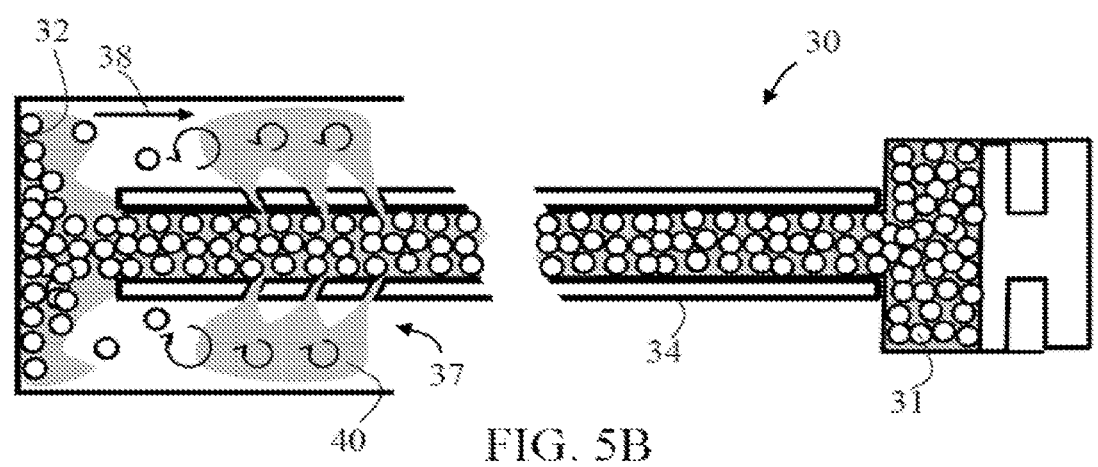

FIGS. 5A-5B schematically illustrate side cut views of exemplary embodiments of an exemplary microcatheter 30 during delivery of embolic material 31 before (FIG. 5A) and after (FIG. 5B) occurrence of a retrograded flow. Microcatheter 30 is sized and configured for delivering embolic material 31 in a small blood vessel towards a target bodily part 32. Microcatheter 30 includes a single lumen 33 surrounded by a tubular wall 34 having an outer diameter and opened at both ends. In some embodiments, tubular wall 34 is sized for unhindered insertion into a small blood vessel, such as a celiac or hepatic artery. In some embodiments, outer diameter of microcatheter 30 is equal to or less than about 2 mm, or equal to or less than about 1 mm. In some embodiments, microcatheter 30 has an external diameter equal to the diameter of a commercially available microcatheter, such as a 2.1 French catheter, or a 2.7 French catheter, or a 2.9 French catheter.

A proximal portion of tubular wall 34 is connectable to a pressure source and to a reservoir configured for containing an infusion suspension of an embolic material 31.

A distal portion of tubular wall ends with a tip 35, enclosing a distal outlet 36. Tubular wall 34 distal portion includes an embolic material flow disruption section 37 configured to disrupt passage of an incoming retrograded (in a general distal direction) flow 38 of the embolic material around tubular wall 34, during continuous delivery of the embolic material 31 from the reservoir to tip 35 and out through distal outlet 36. As shown in FIG. 5B, flow disruption section 37 is configured to diminish, or block, incoming retrograded flow 38 of the embolic material 31, for example, thereby increasing local pressure thereabout or/and creating local turbulence or vortex. In some embodiments, the turbulence or vortex is created by infusion fluid injected or otherwise expelled from the microcatheter, for example, wherein the embolic material 31 is partially or fully filtered from the infusion fluid.

Flow disruption section 37 includes a plurality of openings 39 distributed around or/and along it, each opening is shaped or/and sized to effect passage therethrough of an infusion fluid (such as a viscous fluid) 40, and to block passage therethrough of the embolic material 31. In exemplary embodiments, infusion fluid 40 includes a contrast enhancing material (agent), for example, diluted to a certain degree such as with saline.

One or more opening 39 includes a pore having a cross sectional dimension less than minimal diameter of the embolic material, for example, embolization material (e.g., bead diameter). Such cross sectional dimension is, for example, less than about 500 microns (μm), or, equal to or less than about 100 microns (μall), or, equal to or less than about 40 microns (μall). In exemplary embodiments, the cross section dimension is in a range of between about 20 microns (μm) and about 30 microns (μm), for example, about 28 microns (μm). For example, as shown, each pore is located at end of a channel being angled (wherein the angle is an exemplary range of between about 0 degrees and about 90 degrees) relative to a long axis of lumen 33 or/and relative to a radial axis thereof at a cross section adjacent thereto. In exemplary embodiments, at least two pores are angularly located in different directions such that a first stream of the infusion suspension in immediate vicinity of a first pore at least partially intersects a second stream of the infusion suspension in immediate vicinity of a second pore. Openings 39 or pores may be in any possible form, for example, with circular or rectangular cross section, or as a burst slit (i.e., opened only under chosen pressure or force), or a constantly opened slit. In such exemplary embodiments, the openings 39 or pores have a minimal cross sectional dimension being less than the minimal diameter of the embolic material (e.g., embolization material, (for example, in the form of beads).

In some embodiments, lumen 33 is configured to deliver a suspension of infusion fluid 40 and embolic material 31, for example, in a form of beads. In some embodiments, distal outlet 36 is shaped or/and sized to effect passage therethrough of the infusion suspension of infusion fluid 40 and the embolic material (beads) 31, and at least one side opening 39 is shaped or/and sized to effect passage therethrough of infusion fluid 40, and to block passage therethrough of embolic material (beads) 31, for example, if a cross sectional dimension of the pore in each opening is less than a minimal diameter of the embolic material (beads).

In some embodiments, at least one side opening 39 is shaped or/and sized to effect passage therethrough of infusion fluid 40, and to block passage therethrough of embolic material (beads) 31, during flow of the infusion suspension through distal outlet 36. In some other embodiments, at least one side opening 39 is shaped or/and sized to effect passage therethrough of infusion fluid 40, and to block passage therethrough of embolic material (beads) 31, during conditions when the infusion suspension is blocked or interrupted from flowing through distal outlet 36.

In some embodiments, a total opened cross section of all openings 39 is equal to or greater than a smallest cross section of lumen 33 and distal outlet 36.

In some embodiments, a farthest distal side opening 39 is located within a range of between about 0 mm and about 20 mm, or within a range of between about 0 mm and about 10 mm, or within a range of between about 0 mm and about 5 mm, proximally to distal outlet 36.

Figure 6:
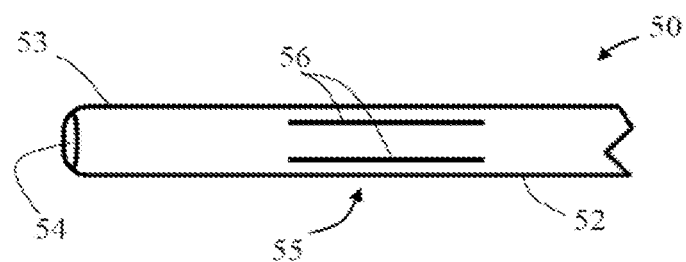
FIG. 6 is a schematic top view of an exemplary embodiment of an embolic material flow disruption section having openings in form of slits, in accordance with some embodiments of the invention.

FIG. 6 schematically illustrates a top view of an exemplary embodiment of an embolic material flow disruption section 55 (included in an exemplary microcatheter 50) having openings in form of slits. Microcatheter 50 is sized and configured for delivering embolic material, for example, including embolization material (e.g., in a form of beads) in a small blood vessel, towards a target bodily part. Microcatheter 50 includes a tubular wall 52 having a distal portion which ends with a tip 53, enclosing a distal outlet 54. Tubular wall 52 distal portion includes an embolic material flow disruption section 55 configured to disrupt passage therethrough of an incoming retrograded flow of the embolic material, for example, during continuous delivery of the embolic material through distal outlet 54. Flow disruption section 55 is configured to block, or/and cause turbulence in, incoming retrograded flow of the embolic material, thereby increasing local pressure thereabout.

Flow disruption section 55 includes a plurality of openings 56 distributed around or/and along it, each opening includes a slit with a gap having a cross sectional dimension (e.g., width) less than minimal diameter of the embolic material. In exemplary embodiments, another cross sectional dimension of this gap (e.g., length) is substantially greater than the minimal diameter of the embolic material. In some embodiments, each opening is shaped or/and sized to effect passage therethrough of an infusion fluid, and to block passage therethrough of the embolic material.

In some embodiments, flow disruption section 55 includes material being firmer than material of other sections of tubular wall 52 distal portion. In exemplary embodiments, flow disruption section 55 is made of a metallic material, a hard polymeric material, or a combination thereof. In exemplary embodiments, flow disruption section 55 is coated with a radiopaque material such as with hydrophilic coating. In exemplary embodiments, flow disruption section 55 is structured with a metal coil, for example, impregnated with solid structure or/and attached to a layer of solid structure.

FIGS. 7A-7B schematically illustrate side cut views of exemplary embodiments of a microcatheter 60 including a plurality of projections, during delivery of embolic material (e.g., embolization material) before (FIG. 7A) and after (FIG. 7B) occurrence of a retrograded flow. Microcatheter 60 is sized and configured for delivering the embolic material, for example, embolization material (e.g., in a form of beads) in a small blood vessel, towards a target bodily part. Microcatheter 60 includes a tubular wall 61 having a distal portion which ends with a tip 62, enclosing a distal outlet 63. In some embodiments, tubular wall 61 is sized for unhindered insertion into a small blood vessel, such as a celiac or hepatic artery.

Tubular wall 61 distal portion includes an embolic material flow disruption section 64 configured to disrupt passage of an incoming retrograded flow of the embolic material, during continuous delivery of the embolic material through distal outlet 63. Flow disruption section 64 is configured to diminish, block, or/and cause turbulence or vortex in, incoming retrograded flow of the embolic material in a distal direction around Tubular wall 61 distal portion adjacent thereto, and optionally increase local pressure thereabout.

Flow disruption section 64 includes a plurality of projections 65 branching out from and distributed around or/and along it. In exemplary embodiments, projections 65 are flexible or/and configured to bend proximally into a straight form along tubular wall 61 distal portion when flow disruption section 64 is passed distally within a closely fitting outer tube. In exemplary embodiments, projections 65 are curled distally towards tip 62 when in a relaxed configuration such as in absence of retrograded flow.

FIGS. 8A-8D schematically illustrate partial side cut views of exemplary embodiments of different exemplary projections of an embolic material flow disruption section. FIG. 8A shows projections 66 in a form of threads angled distally at least when in relaxed configuration, FIG. 8B shows projections 67 in a form of threads angled proximally at least when in relaxed configuration, FIG. 8C shows projections 68 in a form of prongs, and FIG. 8D shows projections 69 in a form of bulges, for example, as a result of a coil wounded over the low disruption section.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

Each of the phrases 'consisting of' and 'consists of', as used herein, means 'including and limited to'.

The phrase 'consisting essentially of', as used herein, means that the stated entity or item (system, system unit, system sub-unit, device, assembly, sub-assembly, mechanism, structure, component, element, or, peripheral equipment, utility, accessory, or material, method or process, step or procedure, sub-step or sub-procedure), which is an entirety or part of an exemplary embodiment of the disclosed invention, or/and which is used for implementing an exemplary embodiment of the disclosed invention, may include at least one additional 'feature or characteristic' being a system unit, system sub-unit, device, assembly, sub-assembly, mechanism, structure, component, or element, or, peripheral equipment, utility, accessory, or material, step or procedure, sub-step or sub-procedure), but only if each such additional 'feature or characteristic' does not materially alter the basic novel and inventive characteristics or special technical features, of the claimed entity or item.

The term 'method', as used herein, refers to steps, procedures, manners, means, or/and techniques, for accomplishing a given task including, but not limited to, those steps, procedures, manners, means, or/and techniques, either known to, or readily developed from known steps, procedures, manners, means, or/and techniques, by practitioners in the relevant field(s) of the disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably.

The term 'about', as used herein, refers to ±10% of the stated numerical value.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or subcombination—in the context or format of a single embodiment, may also be illustratively described and presented in the context or format of a plurality of separate embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A kit for preventing non-target deposition of embolization particles, said kit comprising:
   an entrapping device configured for positioning within a right atrium and for covering an inlet opening of the right atrium, comprising a filter comprising a mesh configured to allow blood flow therethrough while entrapping embolization particles flowing toward the right atrium, thereby preventing the embolization particles from entering the right atrium, and a collapsing mechanism configured to turn the filter into a closed pocket preventing outflow of entrapped embolization particles therefrom; and
   an embolization microcatheter configured for delivering the embolic particles to a target organ tubular wall, said embolization microcatheter comprising a distal outlet and a plurality of side openings distributed around and along a section of a wall of said embolization microcatheter proximally to the distal outlet; wherein said distal outlet is shaped and sized to facilitate delivery of the embolization particles and wherein each of said plurality of side openings is shaped and sized to block passage therethrough of the embolization particles while allowing outflow of fluid.

2. The kit of claim 1, wherein the collapsing mechanism comprises a drawstring threaded around the perimeter of the filter.

3. The kit of claim 1, wherein the mesh has strands with a thickness of 200 micrometers or less.

4. The kit of claim 1, wherein the mesh has strands with a thickness of 100 micrometers or less.

5. The kit of claim 1, wherein the mesh has strands with a thickness of 50 micrometers or less.

6. The kit of claim 1, wherein pores of the mesh have a pore diameter of 100 micrometer or less.

7. The kit of claim 1, wherein pores of the mesh have a pore diameter of diameter of 50 micrometer or less.

8. The kit of claim 1, further comprising a vial containing the embolization particles.

9. The kit of claim 1, wherein the filter has a parachute-like shape.

10. The kit of claim 9, wherein the embolization particles have a diameter in the range of 10-1500 micrometer.

11. The kit of claim 9, wherein the embolization particles have a diameter in the range of 10-500 micrometer.

12. The kit of claim 1, wherein the filter is made of a polymeric material.

13. The kit of claim 12, wherein the polymeric material is selected from the group of polypropylene (PP), polyvinylchloride (PVC), polyamide (nylon), polyurethane, polyester, polyethylene tetraphalate, polyether-ether ketone (PEEK), polyether block amide (PEBA), polytetraflouroethylene (PTFE), or any mixture, blend or combination thereof.

14. The kit of claim 1, wherein the filter is made of metal alloy.

15. The kit of claim 14, wherein the metal alloy is selected from stainless steel, nickel-titanium, platinum or cobalt chrome.

16. The kit of claim 1, wherein the plurality of side openings are in a form of axial slits.

* * * * *